(12) United States Patent
Prais et al.

(10) Patent No.: US 12,295,745 B2
(45) Date of Patent: May 13, 2025

(54) STERILIZED REUSABLE WEARABLE DEVICES AND WEARABLE DEVICE FORMING METHODS IN CONTINUOUS ANALYTE MONITORING

(71) Applicant: ASCENSIA DIABETES CARE HOLDINGS AG, Basel (CH)

(72) Inventors: Eugene Prais, West Milford, NJ (US); Dragan Avirovikj, Stamford, CT (US); Thomas A. J. Mayer, Jr., Glenmoore, PA (US); Cameron M. Young, Tarrytown, NY (US); Igor Y. Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 93 days.

(21) Appl. No.: 17/156,500

(22) Filed: Jan. 22, 2021

(65) Prior Publication Data

US 2021/0228154 A1 Jul. 29, 2021

Related U.S. Application Data

(60) Provisional application No. 63/111,347, filed on Nov. 9, 2020, provisional application No. 62/965,682, filed on Jan. 24, 2020.

(51) Int. Cl.
*A61B 5/00* (2006.01)
*A61B 5/145* (2006.01)
*A61B 90/00* (2016.01)

(52) U.S. Cl.
CPC .......... *A61B 5/6801* (2013.01); *A61B 5/0004* (2013.01); *A61B 5/14532* (2013.01);
(Continued)

(58) Field of Classification Search
CPC ..... A61B 5/6801; A61B 90/08; A61B 5/0004; A61B 5/14532; A61B 2090/0813;
(Continued)

(56) References Cited

U.S. PATENT DOCUMENTS

| 6,175,752 B1 | 1/2001 | Say et al. |
| 7,946,984 B2 | 5/2011 | Brister et al. |

(Continued)

FOREIGN PATENT DOCUMENTS

| CA | 2433144 A1 | 8/2002 |
| CN | 110099708 A | 8/2019 |

(Continued)

OTHER PUBLICATIONS

Hemapriya, D. et al.: "Wearable Medical Devices—Design Challenges and Issues"; 2017 International Conference on Innovations in Green Energy and Healthcare Technologies (IGEHT), IEEE, Mar. 16, 2017, pp. 1-6, XP033243858, DOI: 10.1109/IGEHT.2017.8094096 [retrieved on Nov. 1, 2017].

(Continued)

*Primary Examiner* — David J. McCrosky
*Assistant Examiner* — Meghan R Kumar
(74) *Attorney, Agent, or Firm* — Erise IP, P.A.

(57) ABSTRACT

In one or more embodiments, a continuous analyte monitoring wearable device includes a disposable base unit having a power source and an analyte sensor, and a reusable transmitter unit that includes electronic circuitry configured to bias the analyte sensor, measure current through the analyte sensor, and may even compute analyte values based on measured current through the analyte sensor. The disposable base unit is configured to couple to the reusable transmitter unit and supply electrical power to the electronic (Continued)

circuitry of the reusable transmitter unit for continuous analyte monitoring. Numerous other embodiments are provided.

20 Claims, 25 Drawing Sheets

(52) U.S. Cl.
 CPC ...... *A61B 90/08* (2016.02); *A61B 2090/0813* (2016.02); *A61B 2560/04* (2013.01); *A61B 2562/242* (2013.01); *A61B 2562/247* (2013.01)

(58) Field of Classification Search
 CPC .......... A61B 2560/04; A61B 2562/242; A61B 2562/247; A61B 2560/0214; A61B 2560/0285; A61B 2562/18; A61B 5/002; A61B 5/14865; A61B 2560/045; A61B 2562/164; A61B 5/1473; A61B 5/6802; A61B 5/14514; A61B 5/6813
 See application file for complete search history.

(56) References Cited

U.S. PATENT DOCUMENTS

| 9,931,065 | B2 | 4/2018 | Pryor et al. |
| 2008/0242962 | A1* | 10/2008 | Roesicke ........... A61B 5/14503 600/347 |
| 2009/0102678 | A1 | 4/2009 | Mazza et al. |
| 2009/0257911 | A1* | 10/2009 | Thomas ................. B65D 77/26 422/186 |
| 2011/0190614 | A1* | 8/2011 | Brister ............... A61B 17/3468 600/347 |
| 2012/0123227 | A1 | 5/2012 | Sun et al. |
| 2014/0163338 | A1 | 6/2014 | Roesicke |
| 2016/0022179 | A1 | 1/2016 | Di Resta et al. |
| 2017/0027514 | A1 | 2/2017 | Bierderman et al. |
| 2019/0336049 | A1 | 11/2019 | Shah et al. |
| 2019/0336055 | A1* | 11/2019 | Shah ..................... H04W 52/02 |
| 2019/0357818 | A1 | 11/2019 | Pryor et al. |
| 2021/0030360 | A1* | 2/2021 | Huang ............... A61B 5/14865 |

FOREIGN PATENT DOCUMENTS

| JP | 2005128025 A | 5/2005 |
| JP | 2008246204 A | 10/2008 |
| JP | 2010502520 A | 1/2010 |
| JP | 2010507457 A | 3/2010 |
| JP | 2012511485 A | 5/2012 |
| JP | 2018029983 A | 3/2018 |
| JP | 2019514606 A | 6/2019 |
| WO | 2012068393 A1 | 5/2012 |
| WO | 2018118696 A1 | 6/2018 |

OTHER PUBLICATIONS

International Search Report and Written Opinion of International Application No. PCT/EP2021/051431 mailed Apr. 20, 2021.
Canadian Patent Application 3,165,007, Examination Report issued Jan. 22, 2024.
Taiwan Patent Application 110102474 Official Action and Search Report issued May 2, 2024.
Canadian Patent Application 3,165,007 Examination Report issued Oct. 1, 2024.
Japanese Patent Application 2022-523872, Notice of Reason of Refusal, issued Nov. 27, 2024.
European Patent Application Office Action issued Feb. 3, 2025.
Taiwan Patent Application 110102474 Notice of Allowance issued Feb. 5, 2025.
China Patent Application 202180006098.X, First Office Action, issued Mar. 1, 2025.

* cited by examiner

STERILIZED REUSABLE WEARABLE DEVICES AND WEARABLE DEVICE FORMING METHODS IN CONTINUOUS ANALYTE MONITORING

CROSS-REFERENCE TO RELATED APPLICATION

This application claims priority to, and the benefit of, U.S. Provisional Patent Application No. 62/965,682, entitled "METHODS AND APPARATUS FOR REUSING TRANSMITTER ELECTRONICS OF A CONTINUOUS ANALYTE MONITORING DEVICE" filed Jan. 24, 2020, and U.S. Provisional Patent Application No. 63/111,347, entitled "STERILIZED REUSABLE WEARABLE DEVICES AND WEARABLE DEVICE FORMING METHODS IN CONTINUOUS ANALYTE MONITORING" filed Nov. 9, 2020, each of which is hereby incorporated by reference in its entirety for all purposes herein.

FIELD

The present disclosure relates to continuous analyte monitoring methods, apparatus, and systems.

BACKGROUND

In-vivo continuous analyte monitoring (CAM), such as continuous glucose monitoring (CGM), has become a routine sensing operation, particularly in diabetes care. By providing real-time monitoring of glucose concentrations, therapeutic/clinical actions may be applied in a more timely way and the glycemic condition may be better controlled.

During CGM operation, a biosensor of a CGM wearable device, which is typically inserted subcutaneously, is continuously operated in an environment surrounded by tissue and interstitial fluid. The biosensor inserted under the skin provides a signal to a wireless CGM transmitter of the CGM wearable device, and that signal is indicative of the user's blood glucose level. These measurements may be made automatically many times throughout the day (e.g., every few minutes or at some other suitable interval).

The CGM wearable device may adhere to the outer surface of a user's skin, such as on the abdomen, or the back of the upper arm, while the biosensor is inserted through the skin so as to contact interstitial fluid. The biosensor interacts with the interstitial fluid, generating electrical signals that are proportional to the amount of glucose present in the interstitial fluid. These electrical signals are communicated to the CGM transmitter and may be further communicated to an external device such as a CGM reader device or a smart phone containing a software application, and may be used to make glucose value determinations and display/communicate glucose readings in various desired formats.

Fabricating CGM wearable devices that are both comfortable for patients and cost effective still remains a challenge. As such, improved CGM wearable devices, CGM systems, and CGM methods are desired.

SUMMARY

In some embodiments, a continuous analyte monitoring wearable device is provided. The continuous analyte monitoring wearable device includes a base unit, comprising: a base, at least one power source, and an analyte sensor assembly; and an encapsulation extending over the base and the at least one power source to form an encapsulated base, the encapsulated base including an attachment region configured to allow a reusable transmitter unit to be coupled to, and decoupled from, the encapsulated base, wherein the encapsulated base, at least one power source, and the analyte sensor form a disposable unit, and the disposable unit is sterilized.

In further embodiments, a method of forming a continuous analyte monitoring wearable device is provided. The method includes providing a base having a power source support location, a sensor assembly support location, and a transmitter unit support location; placing at least one power source at the power source support location; placing a sensor assembly including an analyte sensor at the sensor assembly support location; providing an encapsulation layer over the at least one power source, at least a portion of the sensor assembly, and at least a portion of the base, to form a sealed, disposable unit, wherein the sealed, disposable unit is configured to allow a transmitter unit to be attached to, and detached from, the transmitter unit support location; and sterilizing the sealed, disposable unit.

In some additional embodiments, a method of forming a wearable device configured to be used in continuous analyte monitoring is provided. The method includes providing a base having a transmitter unit support location, a power source support location, and a sensor assembly support location, placing at least one power source at the power source support location, placing a sensor assembly including an analyte sensor at the sensor assembly support location, providing an encapsulation portion having an opening, placing the base within the opening of the encapsulation portion such that the base and encapsulation portion form a sealed, disposable base unit, wherein the sealed, disposable base unit is configured to allow a transmitter unit to be attached to and detached from the transmitter unit support location, and sterilizing the sealed, disposable unit.

Other features, aspects, and advantages of embodiments in accordance with the present disclosure will become more fully apparent from the following detailed description, the claims, and the accompanying drawings by illustrating a number of example embodiments and implementations. Various embodiments in accordance with the present disclosure may also be capable of other and different applications, and its several details may be modified in various respects, all without departing from the scope of the disclosure.

BRIEF DESCRIPTION OF THE DRAWINGS

The drawings, described below, are for illustrative purposes and are not necessarily drawn to scale. Accordingly, the drawings and detailed description are to be regarded as illustrative in nature, and not as restrictive. The drawings are not intended to limit the scope of the disclosure in any way.

FIGS. 1H and 1I illustrate side plan views of an alternative embodiment of a wearable device in which a transmitter unit may attach to a disposable base unit at an attachment region of an encasement layer in accordance with embodiments, as provided herein, wherein FIG. 1H illustrates the transmitter unit being detached and FIG. 1I shows the transmitter unit being attached.

DETAILED DESCRIPTION

Figure 1A:
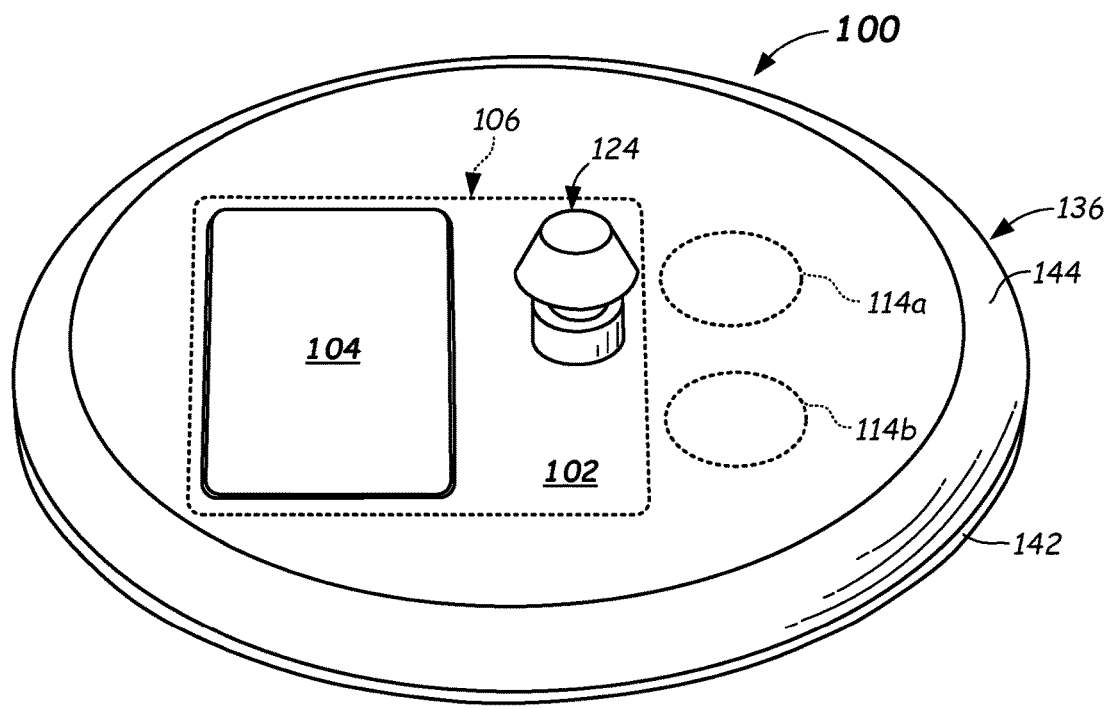
FIGS. 1A and 1B illustrate a top perspective and a side view, respectively, of a continuous analyte monitoring wearable device configured for use in a CAM system in accordance with embodiments provided herein.

In order to more closely monitor a person's glucose level and detect any shift in glucose level, methods, apparatus, and systems for continuous glucose monitoring (CGM) have been developed. While CGM systems generate glucose signals "continuously" during operation, such as continuous electrochemically-generated signals, measurements of the generated glucose signals are typically performed every few minutes, rather than being truly continuous.

CGM systems generally have a wearable portion (a "wearable device") that communicates wirelessly with an external device, such a hand-held monitor or reader, smart phone, or other computing device. The wearable device may be worn for days before being removed and replaced (e.g., after 7 days or more). The wearable device includes a sensor that is inserted so as to be located under the skin. The wearable device also includes circuitry (e.g., analog circuitry) configured to bias the sensor and measuring current signals generated by the sensor when in contact with interstitial fluid. The wearable device further includes processing circuitry configured to process the current signals, such as for determining glucose values based on the measured current signals, as well as for communicating glucose values to an external device of the CGM system, wherein the CGM system is made up of the wearable device and the external device. The wearable device can be adhered to the outer surface of the skin, for example the abdomen, the back of the upper arm, or other suitable body location. Unlike a blood glucose monitoring (BGM) system that measures glucose concentration in blood, CGM systems measure glucose concentration in interstitial fluid (including non-direct capillary blood).

CGM systems may provide frequent measurements of a person's glucose levels without the need for each such measurement to be accompanied by the drawing of a blood sample, such as by finger sticks. CGM systems may still employ occasional finger sticks and the use of a BGM system, such as the Contour NEXT One® by Ascensia Diabetes Care AG of Basel Switzerland, for calibrating the CGM system.

The wearable device of a continuous analyte monitoring system is generally worn for seven days or more, ten days or more, or even 14 days or more, and then is removed and replaced with a new wearable device. Having to replace the wearable device of a continuous analyte monitoring system every seven days or more significantly increases the costs associated with performing continuous analyte monitoring.

Thus, in view of the problems of the prior art, embodiments described herein provide a wearable device for use with an external device during continuous analyte monitoring that includes a disposable portion and a reusable portion. The disposable portion includes the power source for the wearable device, as well as the analyte sensor, while the reusable portion includes electronic circuitry used, for example, to provide a bias to the analyte sensor, measure current signals through the analyte sensor, and/or transmit signals and/or information to the external device. The electronic circuitry of the reusable portion of the wearable device can further compute analyte concentration values, such as glucose concentration values, based upon the measured current signals. These analyte concentration values may be transmitted to the external device in some embodiments.

The reusable portion may also be referred to herein as a reusable transmitter unit. Example circuitry within the transmitter unit may include an analog front end configured to bias the analyte sensor and sense current that passes through the analyte sensor. The front end may include one or more operational amplifiers, current sensing circuitry, etc. Other circuitry within the transmitter unit may include processing circuitry such as analog-to-digital converters for digitizing current signals, memory for storing digitized current signals, a controller such as microprocessor, microcontroller, or the like for computing analyte concentration values based on measured current signals, and transmitter circuitry for transmitting signals and/or analyte concentration values to the external device.

Electronic circuitry is generally the most expensive portion of the wearable device and can last significantly longer than the period in which the wearable device is employed. For example, wearable devices are typically discarded after about seven days or more, while the circuitry within the transmitter unit may last indefinitely in some cases.

The two components most likely to need replacing in a wearable device used for continuous analyte monitoring are the power source (e.g., one or more batteries that power the electrical components of the wearable device) and the analyte sensor. By placing the power source (e.g., battery) and sensor in the disposable portion (also called a "disposable base unit") of the wearable device, the two components most likely to need replacing may be replaced after each use, while the reusable transmitter unit containing the electronics of the wearable device may be reused 10, 20, 50, 100, or even more than 100 times.

For example, in some embodiments, a wearable device for use during continuous analyte monitoring may include a disposable base unit having a sensor assembly and a power source, and a reusable transmitter unit configured to interface with the disposable base unit and receive power from the power source of the disposable base unit. The disposable base unit is configured to be disposed of after a single analyte monitoring period (e.g., after 7-14 days after the start of use, for example), and the reusable transmitter unit is configured to be detached from the disposable base unit after the single analyte monitoring period and re-used with another disposable base unit. The analyte monitoring period as used herein is the elapsed period of time that a sensor of a disposable unit is operable to monitor an analyte. These wearable devices and other embodiments, continuous analyte monitoring systems, as well as methods for making and/or using such wearable devices, are described below with reference to FIGS. 1A-15.

Figure 1B:
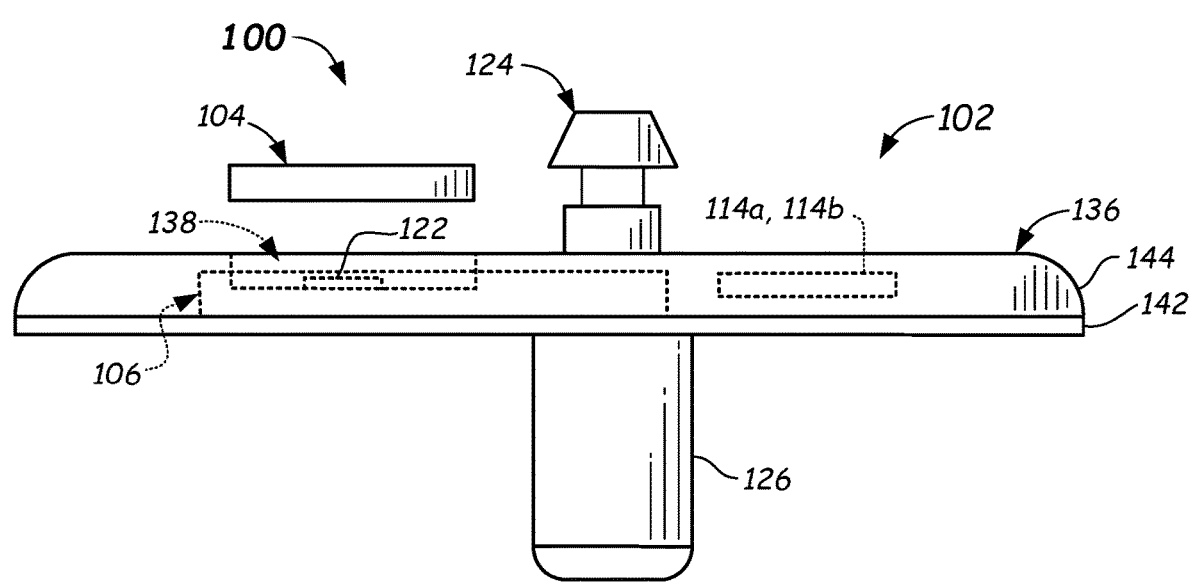

FIGS. 1A and 1B illustrate a top perspective view and a side plan view, respectively, of a wearable device 100 configured to be used during continuous analyte monitoring in accordance with embodiments provided herein. With reference to FIG. 1A, wearable device 100 includes a disposable base unit 102 and a reusable transmitter unit 104 that interfaces with disposable base unit 102. The reusable transmitter unit 104 may be configured to receive electrical power from a power source disposed within disposable base unit 102 and electrical signals from an analyte sensor associated with disposable base unit 102, as described further below. In some embodiments, disposable base unit 102 is configured to be disposed of after a single analyte monitoring period (e.g., 7 days, 10 days, 14 days, or some other suitably-long time period), while reusable transmitter unit 104 is configured to be removed from disposable base unit 102 after the single analyte monitoring period and re-used with a new disposable base unit. For example, transmitter unit 104 may be re-used 2, 5, 10, 50, 100, or even more than 100 times. Example embodiments of disposable base unit 102 and transmitter unit 104 are described below herein.

Figure 1C:
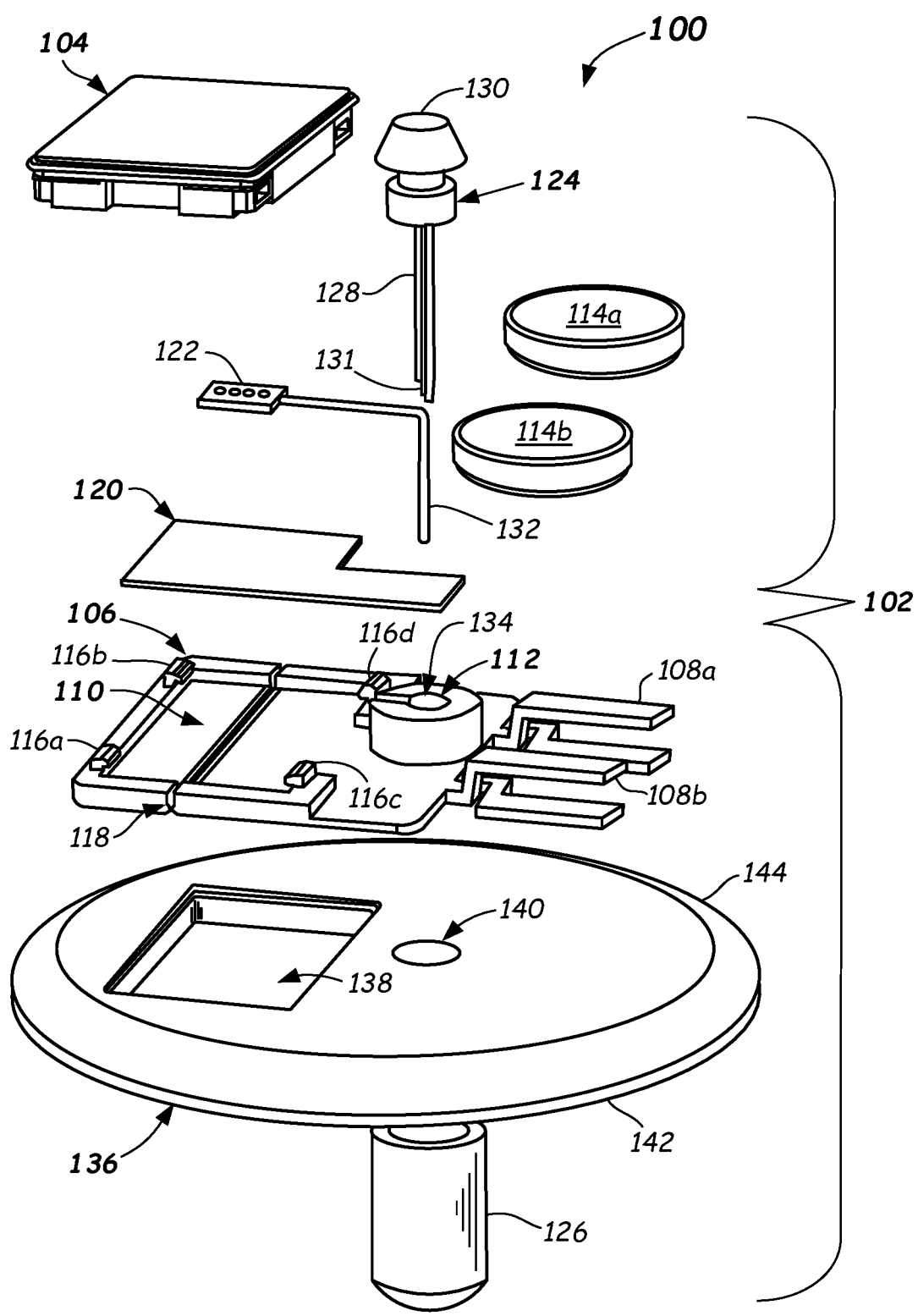
FIG. 1C illustrates an exploded perspective view of a first example embodiment of a wearable device with a disposable base unit and a reusable transmitter unit, with the encapsulation shown as a separate element in perspective, as provided herein.
Figure 1D:
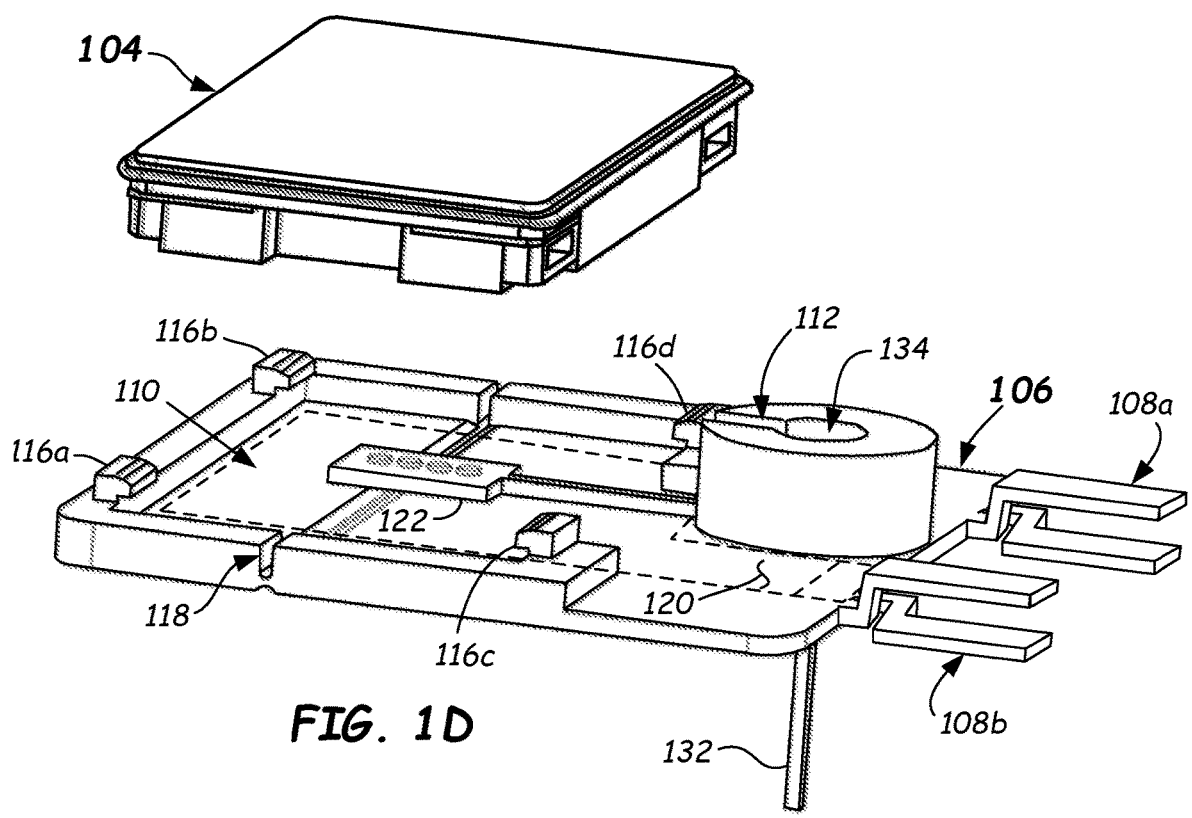
FIG. 1D illustrates an enlarged perspective view of a base and transmitter unit of FIG. 1C coupleable and detachable therefrom, as provided herein.

FIG. 1C illustrates an exploded perspective view of a first example embodiment of disposable base unit 102 and reusable transmitter unit 104 also shown in perspective, as provided herein. With reference to FIG. 1C, disposable base unit 102 includes a base 106 having one or more power source support locations 108a-108b, a transmitter unit support location 110, and a sensor assembly support location 112. FIG. 1D illustrates an enlarged perspective view of the base 106 and the transmitter unit 104 of FIG. 1C.

In some embodiments, base 106 may be formed from a moldable plastic, for example, such as, but not limited to, acrylonitrile butadiene styrene (ABS), polycarbonate, nylon, acetal, polyphthalamide (PPA), polysulfone, polyethersulfone, polyetheretherketone (PEEK), polypropylene, high-density polyethylene (HDPE), and low-density polyethelene (LDPE). Other materials may be used.

Power support locations 108a-108b provide a location for supporting one or more power sources used to supply electrical power to transmitter unit 104. For example, one or more power sources 114a-114b may be positioned at power source support locations 108a, 108b. Power source support locations 108a, 108b may be any suitable shape in top plan view (e.g., rectangular, square, round, etc.) and can include any suitable configuration of electrical contacts that are configured to make electrical contact with the respective poles of the one or more power sources 114a-114b, such as multi-prong connectors shown. Such multi-prong connectors can be formed of any conductive material, such as metal or metalized tape, for example. Further, support locations 108a, 108b may include any suitable configuration of conductive electrical contact traces enabling power connections to the connector 122 from the electrical contacts and thus to the transmitter unit 104.

Figure 1E:
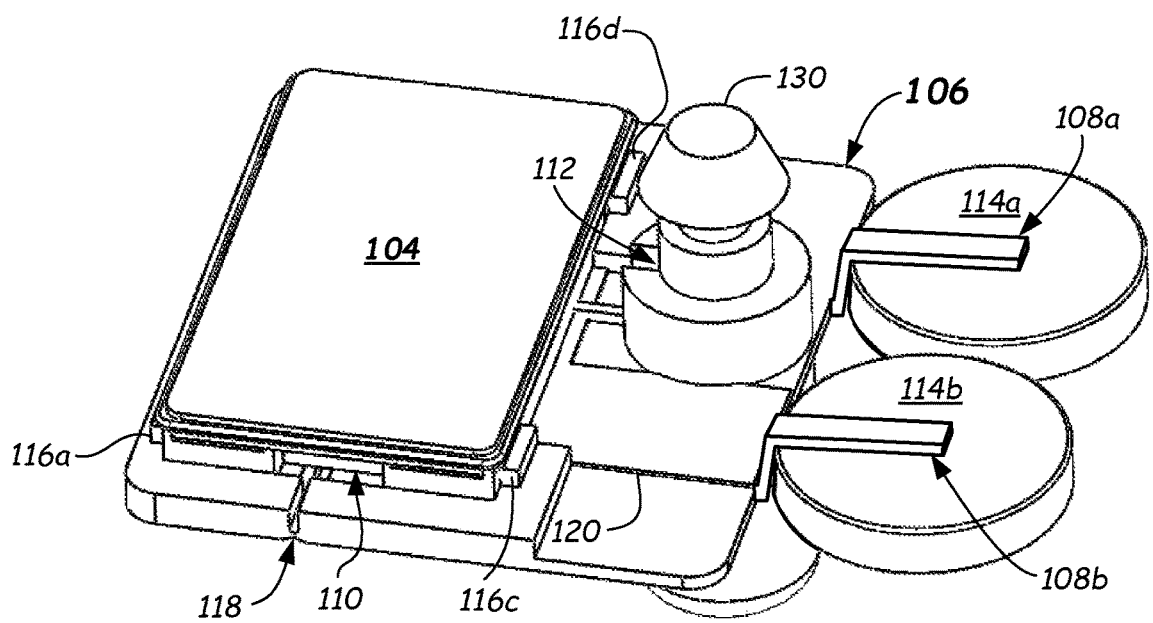
FIG. 1E illustrates an enlarged perspective view of a base and transmitter unit of FIG. 1C with the transmitter unit positioned within a transmitter unit support location and power sources positioned on power source support locations, respectively, of the base, as provided herein.

FIG. 1E further illustrates an enlarged perspective view of base 106 and transmitter unit 104 of FIG. 1C with transmitter unit 104 positioned within transmitter unit support location 110 and power sources 114a and 114b positioned on power source support locations 108*a* and 108*b* (FIG. 1D), respectively, of base 106. In some embodiments power source 114*a* or 114*b* may be a battery, a storage capacitor, a solar cell, a generator, or the like. While two battery power sources 114*a*, 114*b* are shown in FIGS. 1C and 1E, it will be understood that fewer, more and/or different power sources may be used. Further, any suitable construction of electrical contact for securing and connecting to the power sources 114*a* and 114*b* may be used.

Transmitter unit support location 110 is configured to retain transmitter unit 104 coupled or otherwise attached to disposable base unit 102 during continuous analyte monitoring. In some embodiments, transmitter unit support location 110 may include one or more retention features 116*a*-116*d* that interface with and/or press against transmitter unit 104 to retain the coupling of the transmitter unit 104 to base 106, as shown, for example, in FIG. 1E. Fewer, more, and/or different retention features may be used to secure transmitter unit 104 to base 106. Retention features 116*a*-116*d* may include, for example, projections that engage openings in transmitter unit 104, openings that engage projections in transmitter unit 104, magnets, Velcro, surfaces with adhesives, or any other suitable coupling feature. Optionally, projections can be formed on the transmitter unit 104 and can be received in openings formed in the transmitter unit support location 110 of the base.

In some embodiments, transmitter unit support location 110 may include a break location 118 (FIGS. 1C, 1D, and 1E), such as a channel, groove, scribe line, or the like, that allows base 106 to bend and/or break such that retention features 116*a*-116*d* disconnect and/or release transmitter unit 104 when transmitter unit 104 is to be removed from disposable base unit 102/base 106 for re-use with another disposable base unit. Other release and/or break locations or release mechanisms may be used.

A substrate 120, such as a circuit board, a flexible circuit board, etc., may be at least partially located within transmitter unit support location 110 and can include a connector 122 that provides an electrical interface to connect to transmitter unit 104. For example, connector 122 may be electrically connected via conductive paths (not shown) with power sources 114*a*, 114*b* and allow power sources 114*a*, 114*b* to provide electrical power to transmitter unit 104 when transmitter unit 104 is positioned within transmitter unit support location 110. Such conductive paths may be formed in part on the formed on substrate 120 and/or on the base 106.

Sensor assembly support location 112 provides a mounting and support location for an analyte sensor assembly that may include an insertion device 124 and an insertion device cap 126, for example. Insertion device 124 may include an insertion portion 128 coupled to a handle portion 130, for example. Insertion portion 128 of insertion device 124 has a sharpened end 131 (FIG. 1C) that pierces the skin to introduce an analyte sensor 132 into a subcutaneous region of a user as described further below. Insertion portion 128 also may be referred to as an insertion shaft, needle, trocar, sharp or the like.

Insertion portion 128 of insertion device 124 may be made, for example, from a metal such as stainless steel, or a non-metal such as plastic. Other materials may be used. In some embodiments, insertion portion 128 may be, but is not limited to, a round C-channel tube, a round U-channel tube, a stamped sheet metal part folded into a square U-profile, a molded/cast, laser cut or machined metal part with a U-channel profile, or a solid metal cylinder with an etched or ground square U-channel therein. Other insertion portion shapes may be used.

In some embodiments, handle portion 130 of insertion device 124 may be formed from a molded polymer (e.g., plastic), for example, such as, but not limited to, acrylonitrile butadiene styrene (ABS), polycarbonate, nylon, acetal, polyphthalamide (PPA), polysulfone, polyethersulfone, polyether ether ketone (PEEK), polypropylene, high density poly ethylene (HDPE), low density poly ethylene (LDPE), and the like. Other suitable materials may be used.

Handle portion 130 may reside on a top surface of sensor assembly support location 112 of base 106, while insertion portion 128 may extend through a sensor opening 134 (FIG. 1D) in sensor assembly support location 112 of base 106, for example. Analyte sensor 132 is electrically connected to connector 122 of transmitter unit support location 110, which electrically connects analyte sensor 132 to any transmitter unit 104 positioned with transmitter unit support location 110. Electrical conductive paths coupled to connector 122 can further connect to power sources 104*a*, 104*b*.

Figure 1F:
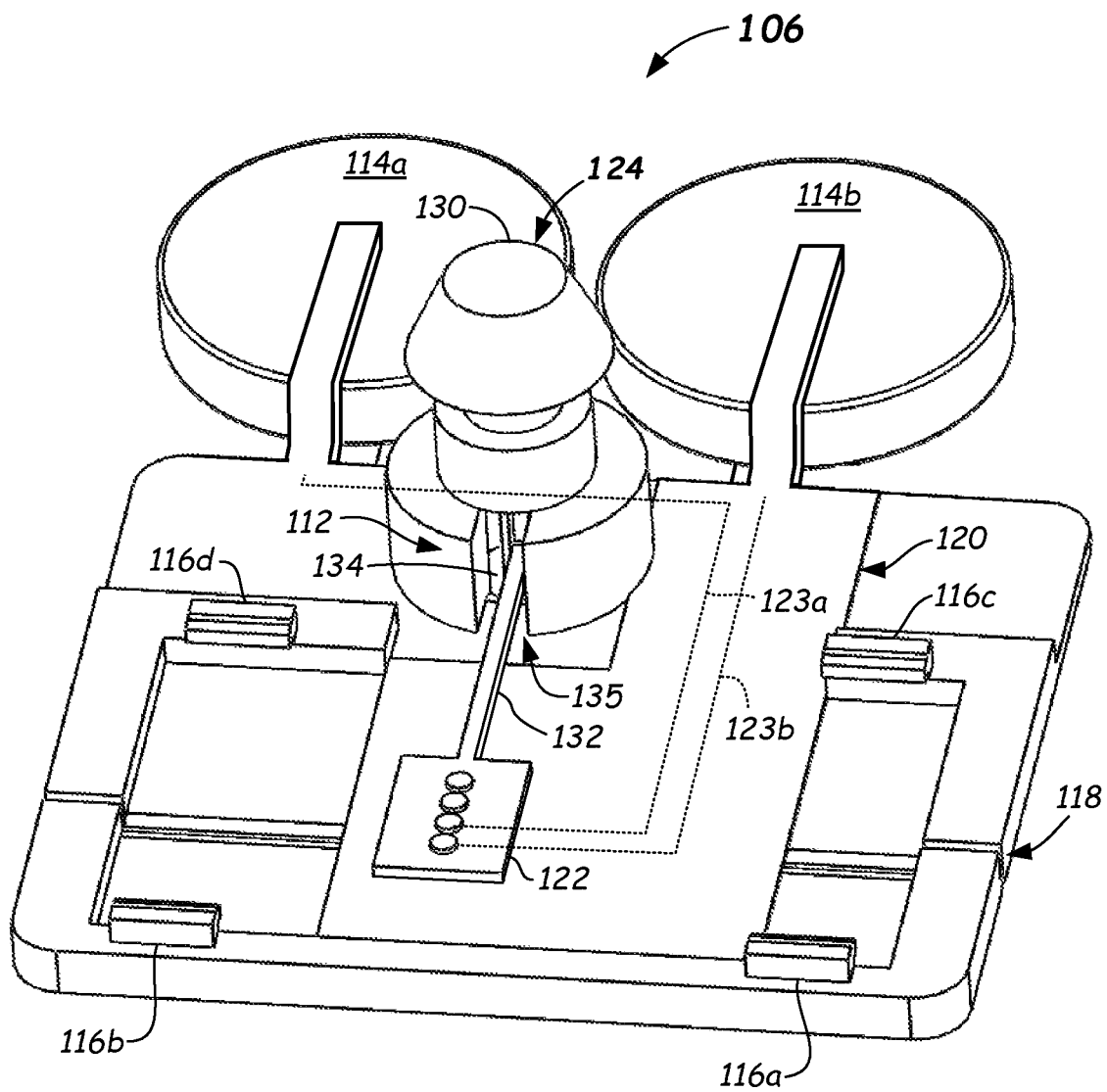
FIG. 1F illustrates a different side perspective view of a sensor coupled to a connector as the sensor extends through a sensor opening at a sensor assembly support location, as provided herein.

FIG. 1F illustrates an alternative side perspective view of sensor 132 coupled to connector 122 as sensor 132 extends through sensor opening 134 in sensor assembly support location 112. As shown, a slot 135 may be provided in sensor assembly support location 112 to facilitate the connection of sensor 132 to connector 122. Connector 122 may be any suitable connector such as an elastomeric connector with metal contacts or another connector type that electrically couples to the analyte sensor 132 and also to the electrical conductors 123*a*, 123*b* providing power from power sources 104*a*, 104*b*.

Referring again to FIGS. 1A-1C, in some embodiments, the base 106 is sealed. For example, an encapsulation layer 136 (shown separately in FIG. 1C) may be formed over base 106 and power sources 114*a*, 114*b* as shown in FIGS. 1A-1B. In some embodiments, the encapsulation layer 136 may include an opening 138 formed therein that allows transmitter unit 104 to be installed in and/or removed from transmitter unit support location 110 of base 106 through the opening 138. In other embodiments, transmitter unit 104 may sit on top of (or otherwise attach to) encapsulation 136 as described further below in FIGS. 1H-1I. In some embodiments, encapsulation layer 136 creates a waterproof seal around base 106 and its internal components, sealing against sensor assembly support location 112 (while leaving an opening 140 (FIG. 1C) for insertion device 124 to extend through base 106 into insertion device cap 126). Connector 122 may remain exposed within transmitter unit support location 110 so transmitter unit 104 may make electrical connection to power sources 114*a*, 114*b* and sensor 132, providing electrical power and current signals from sensor 132 to transmitter unit 104, respectively.

The encapsulation layer 136 may be formed from a single layer or multiple layers. For example, the encapsulation layer 136 may be formed from one or more layers of liquid silicone rubber (LSR), a thermoplastic elastomer (TPE), or the like. Other suitable casting or molding materials may be used. In some embodiments, encapsulation layer 136 may be formed at a temperature of less than 100° C., and in some embodiments at a temperature of less than 80° C. In the embodiment of FIGS. 1A-C, encapsulation layer 136 may be formed from two layers. For example, a bottom, pre-mold encapsulation layer 142 is provided on which base 106 is positioned. Substrate 120 may be positioned within transmitter unit support location 110 with connector 122, and sensor assembly components such as insertion device 124 and sensor 132 may be positioned within sensor assembly location 112 (with sensor 132 connected to connector 122). Power source 114a and/or 114b may be positioned on power source support location 108a, and/or 108b. Thereafter, a top encapsulation layer 144 may be formed over base 106 and power sources 114a, 114b, while leaving opening 138 (or another attachment region) that allows transmitter unit 104 to be attached to, detached from, inserted in and/or removed from base 106. Additional methods for assembling the disposable base unit 102 are described further below with reference to FIGS. 7-9.

Figure 1G:
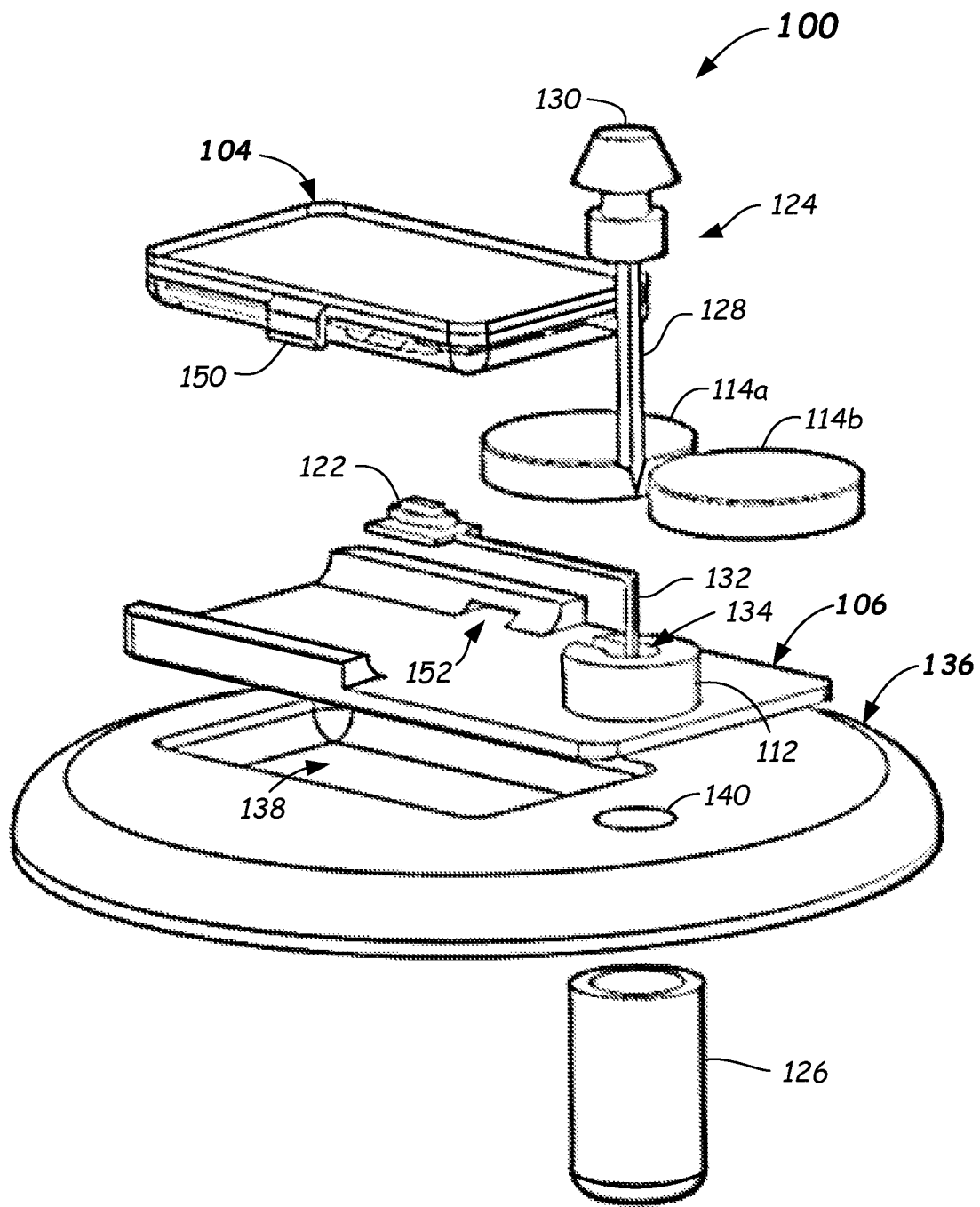
FIG. 1G illustrates an exploded view of an alternative embodiment of wearable device including a disposable base and reusable transmitter unit, as provided herein.

FIG. 1G illustrates an alternative embodiment of base 106 and transmitter unit 104 provided herein. In the embodiment of FIG. 1G, transmitter unit 104 includes two retention features (only retention feature 150 is shown) that interface with corresponding retention features on base 106 (only retention feature 152 is shown). Other retention feature numbers, types and/or locations may be used.

The retention features described herein secure reusable transmitter unit 104 within disposable base unit 102 during continuous analyte monitoring, while allowing the transmitter unit 104 to be removed and reused after a continuous analyte monitoring period. For example, reusable transmitter unit 104 may be configured to interface with disposable base unit 102 so as to receive power from power source 114a and/or 114b of disposable base unit 102. Disposable base unit 102 may be configured to be disposed of after a single analyte monitoring period, while reusable transmitter unit 104 may be configured to be removed from disposable base unit 102 after the single analyte monitoring period and re-used in another disposable base unit. In some embodiments, the single analyte monitoring period may be at least 7 to 10 days (e.g., up to 14 days or longer). Transmitter unit 104 may be removed from a disposable base unit 102 and reused (e.g., 5, 10, 20, 50, 100 or more times), each time with a new disposable base unit that includes a new sensor and a new power source.

Figure 1H:
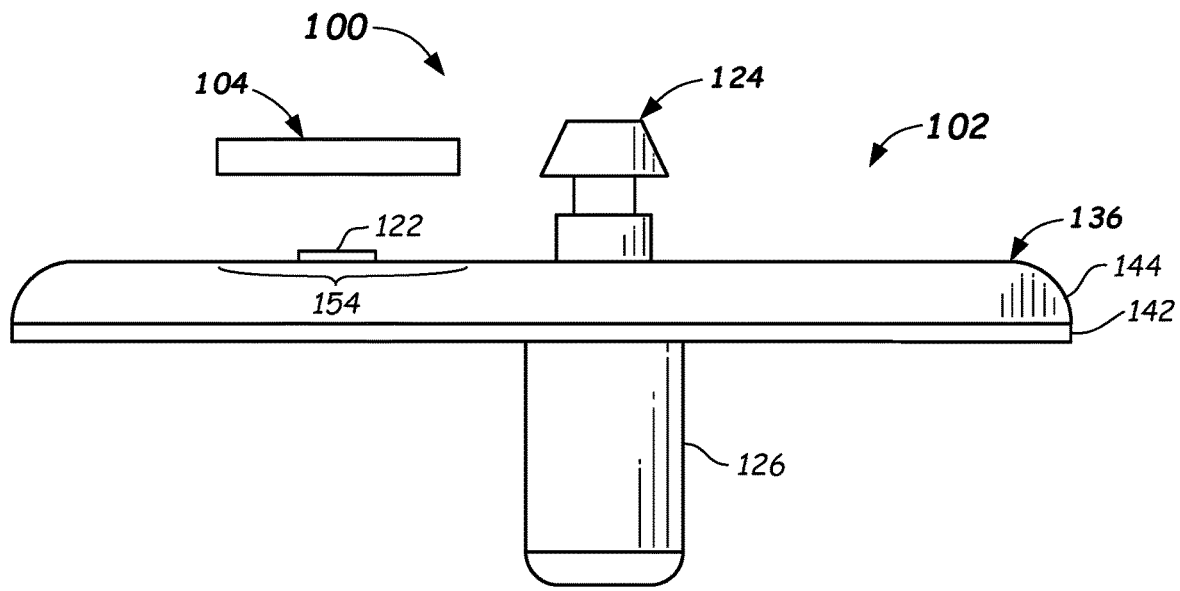
Figure 1I:
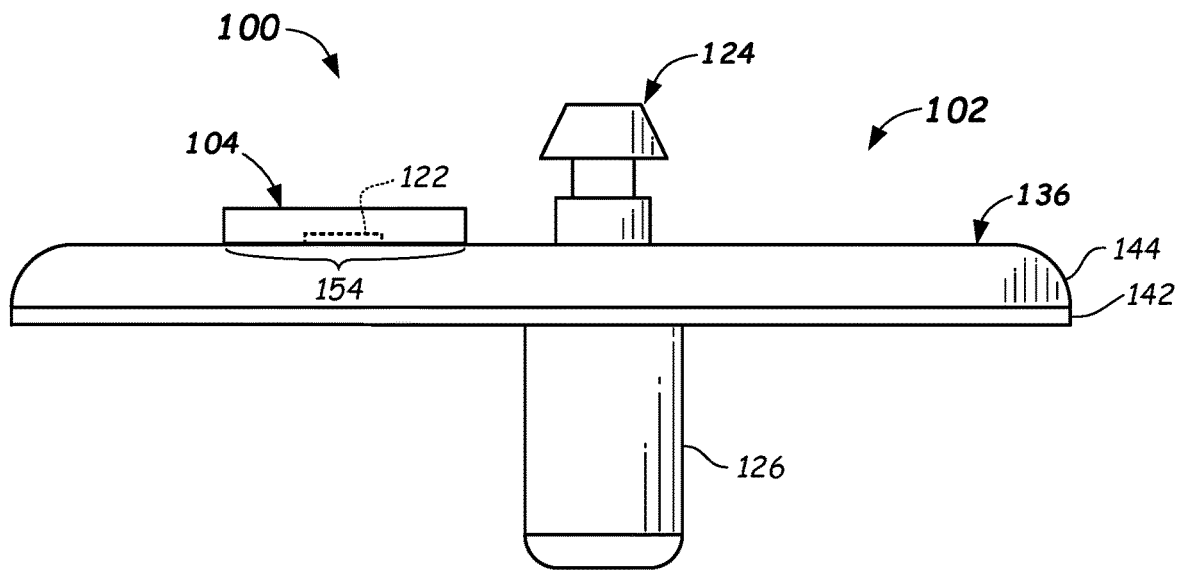

FIGS. 1H and 1I illustrate side views of an alternative embodiment of wearable device 100 in which transmitter unit 104 may attach to disposable base unit 102 at an attachment region 154 of encasement layer 136 in accordance with embodiments provided herein. In such an embodiment, transmitter unit 104 may reside on a top of encasement layer 136, for example. In other embodiments, transmitter unit 136 may attach to an attachment region (not shown) on a bottom of encasement layer 136.

Figure 2:
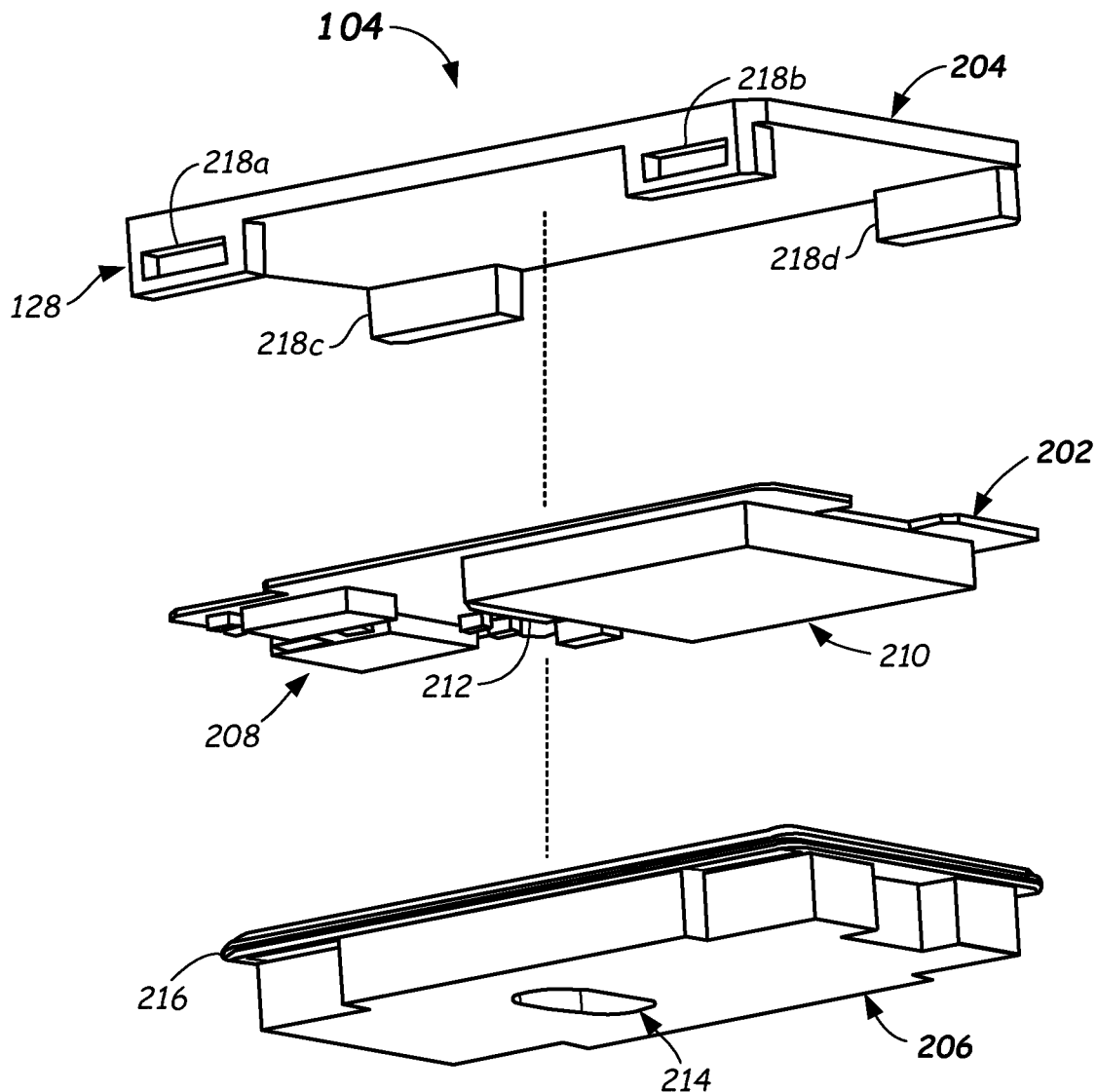
FIG. 2 illustrates an exploded view of an example transmitter unit and base according to embodiments, as provided herein.

FIG. 2 is an exploded view of an example transmitter unit 104 according to embodiments provided herein. With reference to FIG. 2, transmitter unit 104 can include a substrate 202 that couples to top cover 204 prior to forming a bottom cover 206 (e.g., which can be an overmold portion) to cover and seal the substrate 202 and any electrical or electronic components coupled to or formed thereon. Substrate 202 may be a circuit board, a flexible circuit board, or another mounting location for electronic circuitry used within the transmitter unit 104.

In some embodiments, the transmitter unit 104 may include an analog front end 208 configured to apply a voltage to analyte sensor 132 and to sense current flow through analyte sensor 132. Transmitter unit 104 also may include processing circuitry 210 for processing current signals sensed by analog front end 208 and transmitting signals and/or information to an external device. For example, in some embodiments, processing circuitry 210 may convert analog current signals to digital current signals, store current signals, calculate analyte concentration values based on current signals, transmit current signal and/or analyte concentration information to an external device (e.g., an external CGM device), or the like. In some embodiments, processing circuitry 210 may include a processor such as a microcontroller, a microprocessor, etc., memory, analog to digital converters, transmitter circuitry, and the like. Analog front end 208 and processing circuitry 210 may perform other, fewer, and/or more functions.

In an example CGM embodiment, processor circuitry 210 may include a processor, a memory coupled to the processor, and transmitter circuitry coupled to the processor. The memory may include computer program code stored therein that, when executed by the processor, causes the transmitter unit 104 and wearable device 100 to (a) measure glucose signals using a glucose sensor; (b) compute glucose values from the measured glucose signals; and (c) communicate the glucose values to an external device communicatively coupled, such as by Bluetooth or other wireless communication protocol, to the wearable device 100. For example, current sensing circuitry in transmitter unit 104 coupled to the sensor 132 through connector 122 (and interface 212 described below) may measure glucose (current) signals produced by sensor 132. Sampling circuitry may be coupled to the current sensing circuitry and configured to generate digitized glucose signals from the measured glucose signals. These digitized glucose signals may then be used to determine glucose values that are transmitted to an external CGM device for communication (e.g., display) to a user. Optionally, raw signals may be sent and external CGM device may generate digitized glucose signals from the transmitted signals.

Substrate 202 may also include an interface 212 configured to interface with connector 122 of base unit 102 when transmitter unit 104 is positioned at the transmitter unit support location 110 of base 106. An opening 214 in bottom cover 206 may be provided to allow interface 212 to couple with connector 122 of base unit 102, for example. In some embodiments, analog front end 208 may couple to sensor 132 through interface 212 and connector 122 of base unit 102. Likewise, analog front end 208 and processing circuitry 210 may receive electrical power from power source 114a and/or 114b of base unit 102 through connector 122 and interface 212.

In some embodiments, top cover 204 may be a pre-molded base into which substrate 202 is positioned prior to formation of bottom cover 206 (e.g., by a molding process). Alternatively, bottom cover 206 may be a pre-molded base into which substrate 202 is positioned prior to formation or addition of top cover 204. Other assembly processes may be used.

In some embodiments top cover 204 and/or bottom cover 206 may be formed from a single layer or multiple layers. For example, the top cover 204 and/or bottom cover 206 may be formed from one or more layers of liquid silicone rubber (LSR), a thermoplastic elastomer (TPE), or the like. Other materials may be used such as, but not limited to, acrylonitrile butadiene styrene (ABS), polycarbonate, nylon, acetal, polyphthalamide (PPA), polysulfone, polyethersulfone, polyether ether ketone (PEEK), polypropylene, high density poly ethylene (HDPE), low density poly ethylene (LDPE), and the like. Other suitable materials may be used.

In some embodiments, top cover 204 and/or bottom cover 206 may be formed at a temperature of less than 100° C., and in some embodiments at a temperature of less than 80° C., so as not to damage electronics therein. Top cover 204 and bottom cover 206 may seal substrate 202, analog front end 208, and processing circuitry 210 (e.g., so that transmitter unit 104 is waterproof, with only the interface 212 being exposed).

In some embodiments, bottom cover 206 may include a sealing member 216, such as a lip or similar feature, configured to seal against a sidewall of opening 138 of base unit 102 (see also FIG. 4E below), such that transmitter unit 104 and base unit 102 form a sealed unit when transmitter unit 104 is positioned within base unit 102. In some embodiments, top cover 204 may include one or more retention features 218a-218d configured to interface with retention features within transmitter unit support location 110 (e.g., one or more of retention features 116a-116d, for example). Such retention features may couple and hold transmitter unit 104 securely to base unit 102 during use, and keep connector 122 in contact with interface 212. In other embodiments, top cover 204 may include a sealing member and/or bottom cover 206 may include one or more retention features.

Figure 3A:
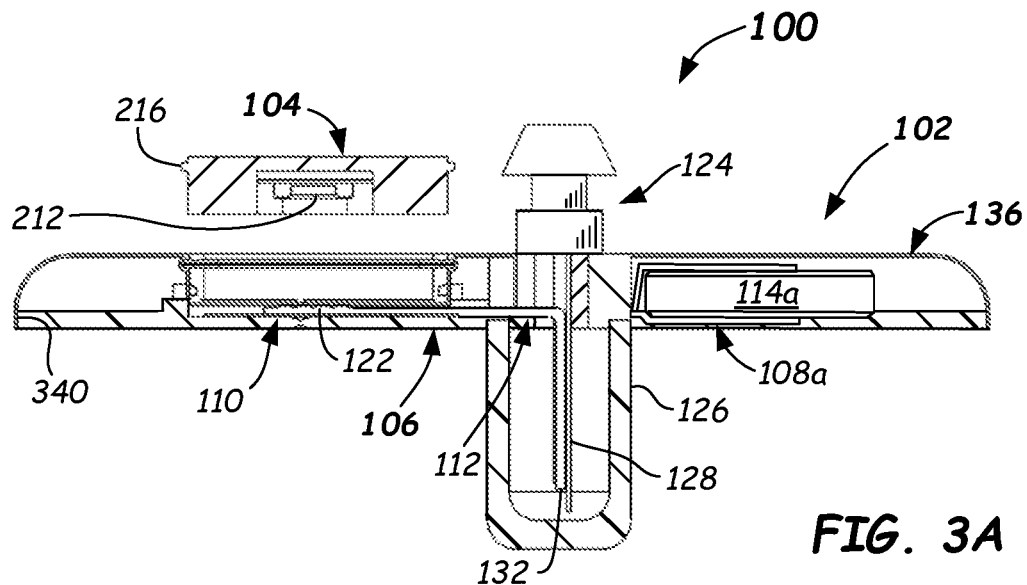
FIG. 3A illustrates a cross-sectioned side view of a wearable device prior to inserting a transmitter unit into a base unit in accordance with some embodiments.
Figure 3B:
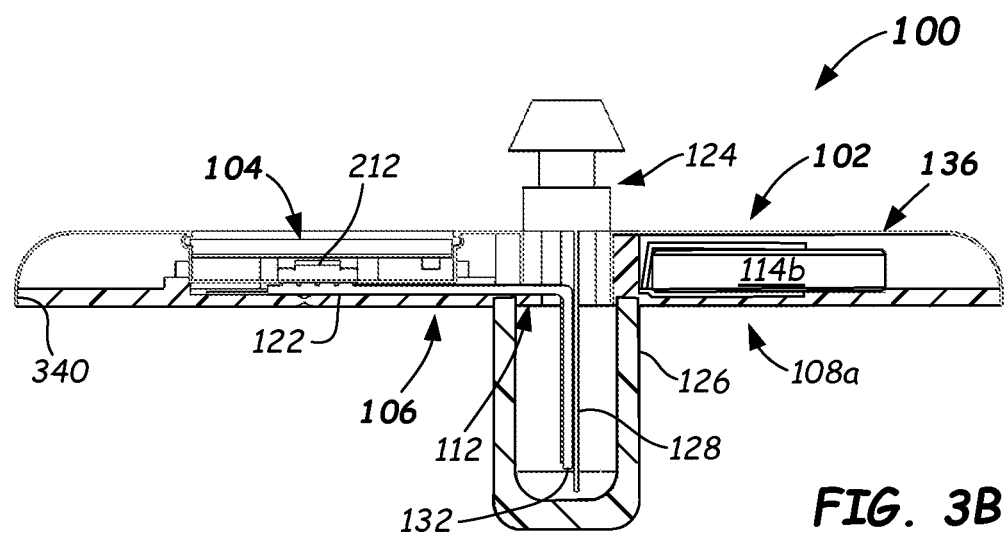
FIG. 3B illustrates a cross-sectioned side view of a wearable device after insertion of a transmitter unit into a base unit in accordance with some embodiments.

FIG. 3A is a cross-sectioned side view of wearable device 100 prior to inserting transmitter unit 104 into base unit 102 in accordance with some embodiments. FIG. 3B is a cross-sectioned side view of the wearable device 100 after insertion of transmitter unit 104 into base unit 102 in accordance with some embodiments. As described, both transmitter unit 104 and base unit 102 may be sealed units (e.g., waterproof), with only interface 212 of transmitter unit 104 and connector 122 of base unit 102 being left exposed. Once transmitter unit 104 is inserted into base unit 102, connector 122 and interface 212 may also be sealed from any external environment, such as by sealing member 216.

Because transmitter unit 104 may receive electrical power from base unit 102 (through connector 122 and interface 212), transmitter unit 104 does not need a separate power source. As such, transmitter unit 104 may be removed and used repeatedly with other new disposable base units when the disposable base unit 102 is exchanged at the end of the analyte monitoring period.

Figure 4A:
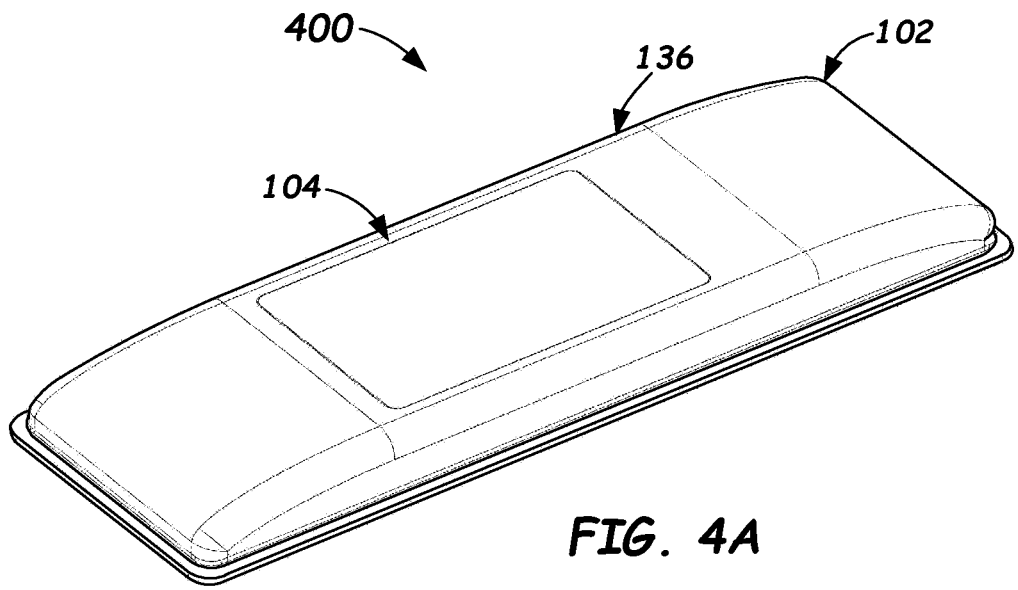
FIGS. 4A and 4B illustrate a top perspective view and an exploded side perspective view, respectively, of another example wearable device, as provided herein.
Figure 4B:
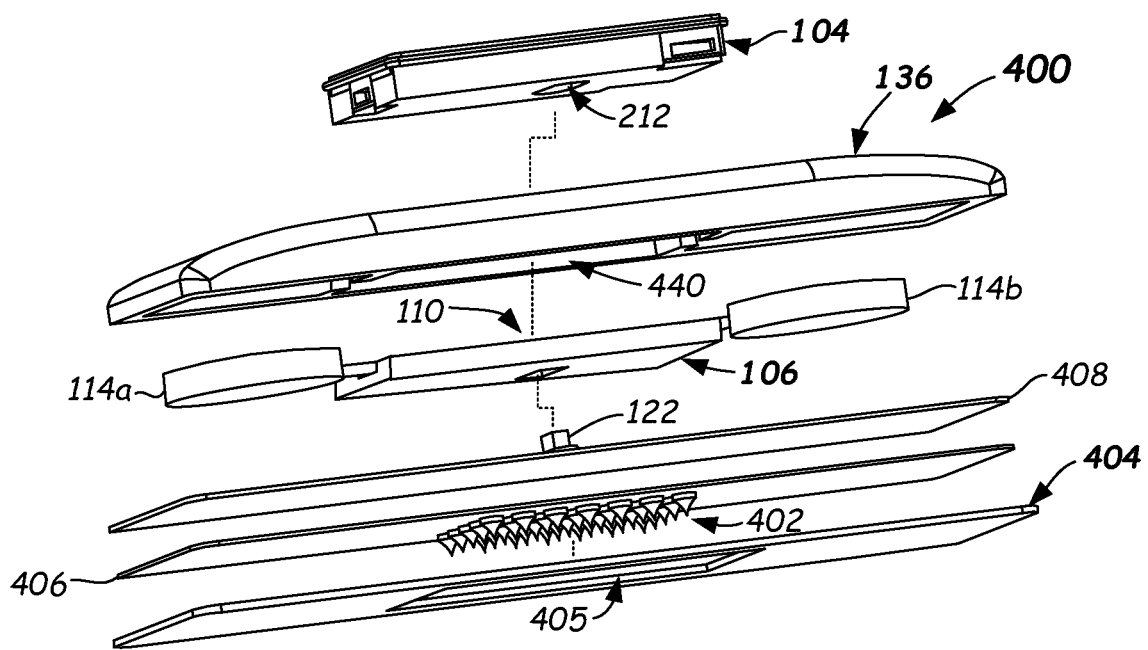

Base unit 102 and/or transmitter unit 104 may be any suitable shape (e.g., round, oval, square, rectangular, or the like). For example, FIGS. 4A and 4B illustrate a top perspective view and an exploded perspective view, respectively, of example wearable device 400 provided herein. Wearable device 400 has a primarily rectangular shape, and is sized and shaped to resemble a medical bandage. In this case, base unit 102 is rectangular. Transmitter unit 104 may be any suitable shape. As with the other embodiments described herein, base unit 102 is disposable and transmitter unit 104 is reusable. That is, in some embodiments, base unit 102 is configured to be disposed of after a single analyte monitoring period, while transmitter unit 104 is configured to be removed from base unit 102 and re-used many times with other (new) base units that can be exact copies of base unit 102.

Now with reference to FIGS. 4A and 4B, in some embodiments, wearable device 400 may employ a sensor assembly 402 including one or more microneedles, such as an array of microneedles shown. Fewer or more microneedles may be used. Wearable device 400 includes a bottom member 404 having an opening 405 through which microneedles extend. Bottom member 404 may be formed from any suitable material such as Liquid silicone rubber (LSR), thermoplastic elastomer (TPE), acrylonitrile butadiene styrene (ABS), polycarbonate, nylon, acetal, polyphthalamide (PPA), polysulfone, polyethersulfone, polyether ether ketone (PEEK), polypropylene, high density poly ethylene (HDPE), low density poly ethylene (LDPE), and the like. Other suitable materials may be used. Bottom member 404 may include an adhesive, such as a pressure sensitive adhesive 439 (see FIG. 4D), used to secure wearable device 400 to the skin of a user.

Sensor assembly 402 comprising microneedle array may be formed on a suitable substrate 406, such as plastic or a similar substrate, and may be attached and electrically coupled to a circuit board 408 (e.g., a flexible circuit board) and bottom member 404 by any suitable means such as by adhesive. Power source 114a and/or 114b may be coupled to circuit board 408 via a base 106 and coupling 122, which may include suitable electrical contacts thereon configured to secure power source 114a and/or 114b and provide power to the circuit board 408. Base 106 may be received in opening 440 as shown in FIG. 4E.

Circuit board 408 may include connector 122 that is coupled to microneedle array 402 and also to power source 114a and/or 114b. Connector 122 is further configured to interface with interface 212 of transmitter unit 104 to provide electrical power to transmitter unit 104 when transmitter unit 104 is installed within base unit 102. Additionally, connector 122 allows transmitter unit 104 to bias microneedle array 402 and sense current flow through one or more microneedles. Transmitter unit 104 may calculate analyte levels within interstitial fluid using the sensed current flow, as described previously.

Figure 4C:
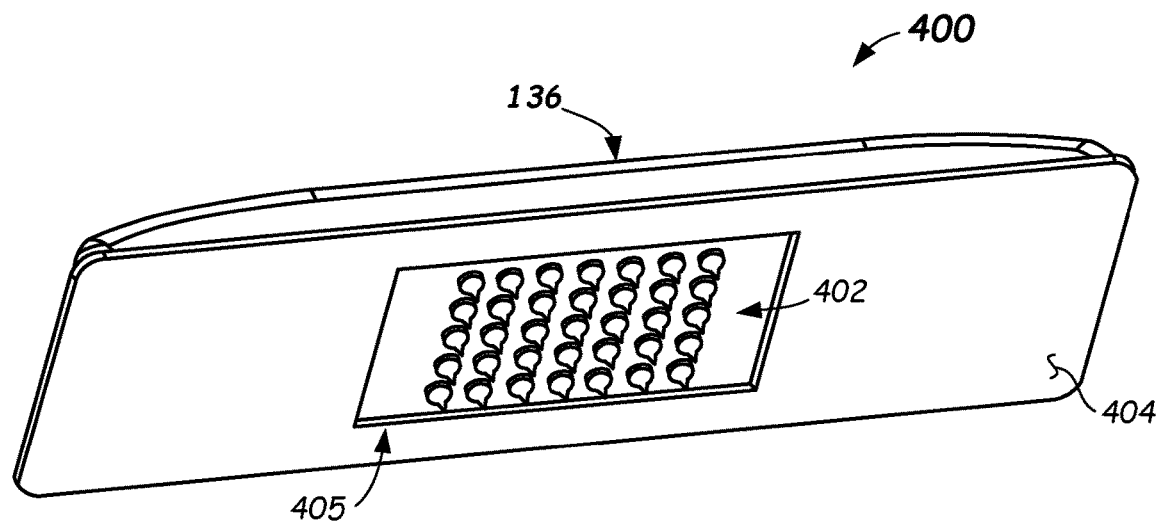
FIG. 4C illustrates a bottom perspective view of another wearable device, as provided herein.
Figure 4D:
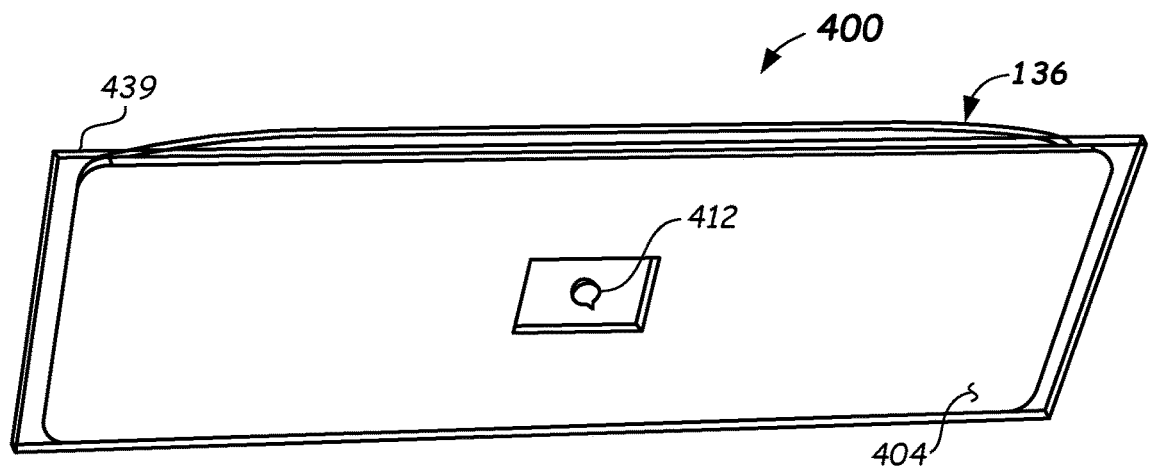
FIG. 4D illustrates a bottom perspective view of an alternative embodiment of a wearable device in which a single microneedle is employed in accordance with embodiments, as provided herein.

FIG. 4C illustrates a bottom perspective view of wearable device 400 in accordance with embodiments provided herein. FIG. 4D illustrates a bottom view of an alternative embodiment of wearable device 400 in which a single microneedle 412 is employed and a transparent tape 439 has been applied that is used to secure the wearable device to the user's skin. FIG. 4E illustrates an enlarged portion of wearable device 400 illustrating transmitter unit 104 inserted within base unit 102 and including a microneedle array 402 in accordance with embodiments provided herein.

Figure 4E:
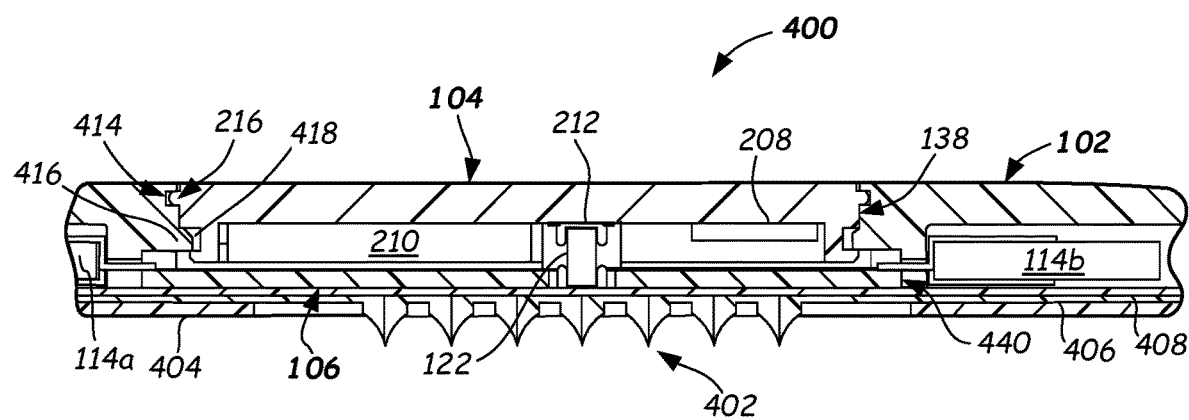
FIG. 4E illustrates an enlarged and cross-sectioned view of a portion of the wearable device of FIG. 4A illustrating a transmitter unit inserted within a base unit in accordance with embodiments, as provided herein.

As shown in FIG. 4E, in some embodiments, transmitter unit 104 may include sealing member 216 (e.g., a sealing bead or lip) that interfaces with a receiving surface 414, such as a groove or similar feature, in a sidewall of opening 138 (FIGS. 1C and 4E) within base unit 102. In this manner, base unit 102 and transmitter unit 104 may form a sealed unit (protecting connector 122 and/or interface 212 from liquids, for example).

FIG. 4E also shows a cross-sectioned side view illustrating that a retention feature 416 of base unit 102 may interface with a corresponding retention feature 418 of transmitter unit 104 to securely hold transmitter unit 104 within opening 138 of base unit 102. The retention features 416 and/or 418 shown may also ensure that connector 122 is held securely within interface 212 during use. Fewer or more retention features may be used (e.g., 2, 3, 4 or more, such as retention features 116a-116d previously described). In some embodiments, transmitter unit 104 may be used in base units that have different shapes. For example, transmitter unit 104 may be used in a round base unit at one time period and then re-used with a rectangular base unit, or vice versa. Also shown in FIG. 1E is that the base 106 is received in opening 440 below opening 138 and secured therein by circuit board 408.

Figure 5:
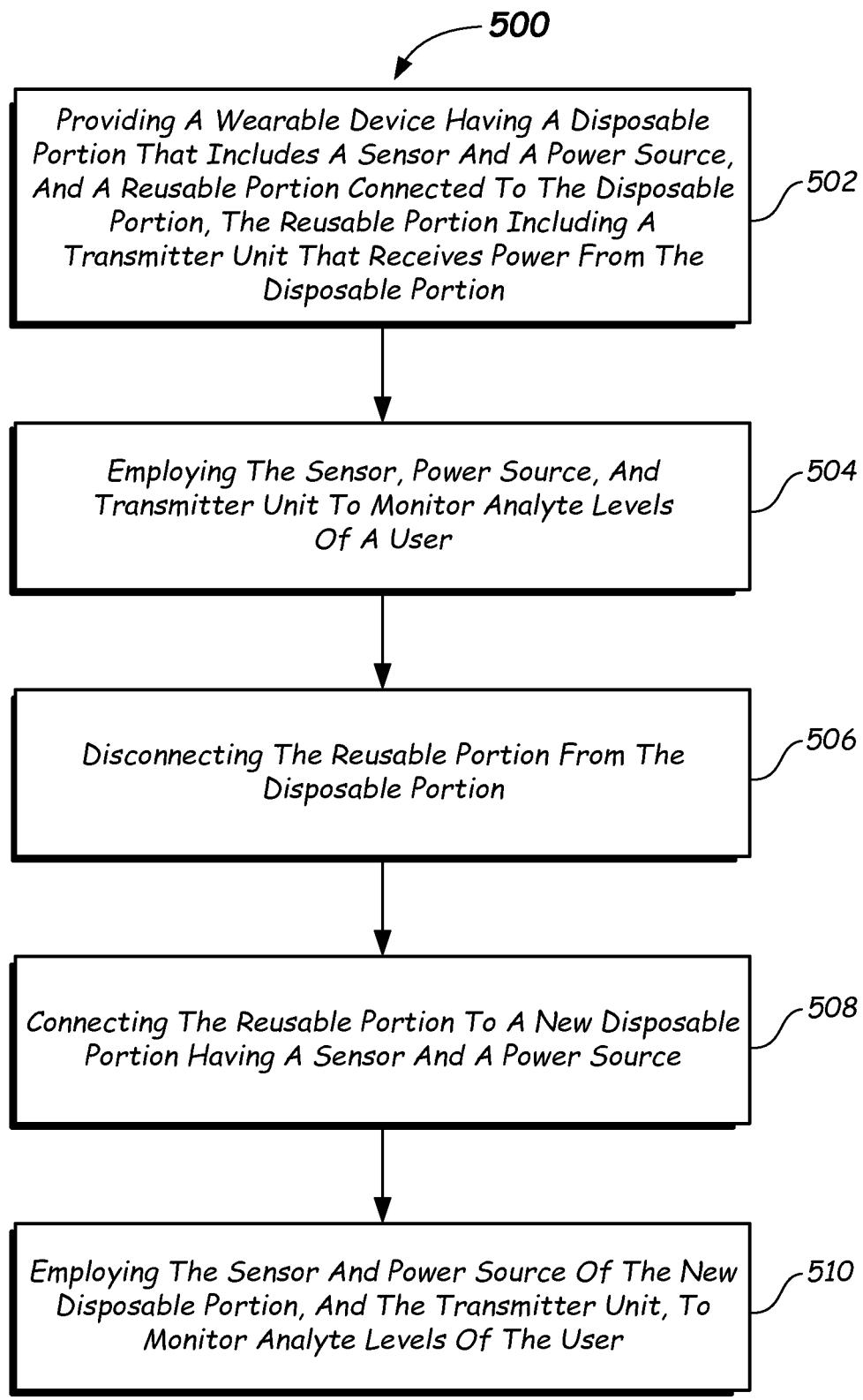
FIG. 5 illustrates a flowchart of an example method for continuous analyte monitoring in accordance with embodiments provided herein.

FIG. 5 is a flowchart of an example method 500 for continuous analyte monitoring in accordance with embodiments provided herein. With reference to FIG. 5, method 500 begins in block 502 in which a wearable device is provided having a disposable portion that includes a sensor and a power source and a reusable portion connected to the disposable portion, the reusable portion including a transmitter unit that receives power from the disposable portion. For example, wearable device 100 or 400 may be provided in which disposable base unit 102 includes a sensor (e.g., an analyte sensor, a microneedle, a microneedle array, etc.) and power source (e.g., a battery or other power source). Reusable transmitter unit 104 may interface with disposable base unit 102 and receive power from base unit 102.

In block 504, the sensor, power source, and transmitter unit are employed to monitor analyte levels of a user. For example, after sensor 132 is inserted into a user, sensor 132, power sources 114a and/or 114b and transmitter unit 104 may be employed to monitor analyte levels of the user during a continuous analyte monitoring process (e.g., for approximately seven to 21 days, for example). Following analyte monitoring, the wearable device may be detached from the user, including the analyte sensor 132. In block 506, the reusable portion of the wearable device is disconnected from the disposable portion of the wearable device. For example, transmitter unit 104 may be removed from base unit 102, and base unit 102 may be discarded. In general, transmitter unit 104 may be disconnected from base unit 102 before or after base unit 102 is removed from the user. Thereafter, in block 508, the reusable portion of the wearable device is connected to a new disposable portion. For example, transmitter unit 104 may be disconnected from base unit 102 and inserted into or otherwise coupled to a new base unit 102 (e.g., having a new power source and new analyte sensor). In block 510, the sensor and power source of the new disposable portion, and the transmitter unit, may be employed to monitor analyte levels of the user. In some embodiments, transmitter unit 104 may be used with at least 10 different sensors and power sources. Transmitter unit 104 may be coupled to base unit 102 before or after base unit 102 is attached to the user.

Figure 6:
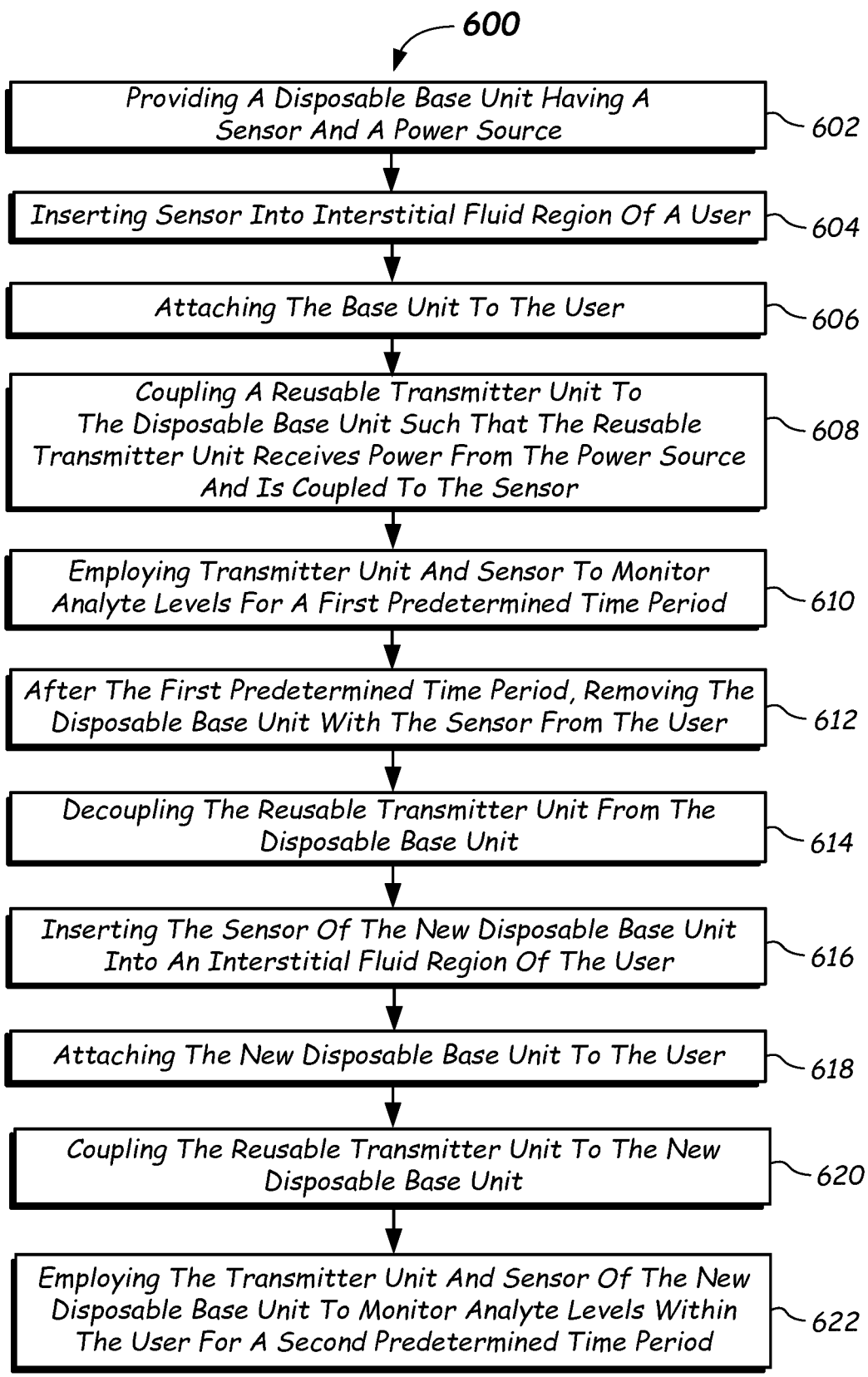
FIG. 6 illustrates a flowchart of another example method for continuous analyte monitoring in accordance with embodiments provided herein.

FIG. 6 is a flowchart of another example method 600 for continuous analyte monitoring in accordance with embodiments provided herein. With reference to FIG. 6, method 600 begins in block 602 in which a disposable base unit having a sensor and a power source is provided (e.g., disposable base unit 102 having sensor 132). Thereafter, in block 604, the sensor is inserted into an interstitial fluid region of a user, and in block 606, the base unit is attached to the user (e.g., via an adhesive on the bottom of the wearable device). In block 608, a reusable transmitter unit is coupled to the disposable base unit such that the reusable transmitter unit receives power from the power source and is coupled to the sensor (e.g., reusable transmitter unit 104 is attached to disposable base unit 102 and receives power and sensor signals through connector 122). The reusable transmitter unit 104 may be attached to the disposable base unit 102 before or after the sensor 132 is inserted into an interstitial fluid region of the user. In block 610, the transmitter unit and sensor are employed to monitor analyte levels within the user for a first predetermined time period. For example, the transmitter unit 104 and sensor 132 may be used to monitor glucose or another analyte level for 7, 10, 14 or another number of days.

After the first predetermined time period, method 600 includes removing the disposable base unit with the sensor from the user (block 612) and decoupling (detaching) the reusable transmitter unit from the disposable base unit (block 614). For example, the transmitter unit 104 may be decoupled from the base unit 102, and the base unit 102 may be discarded. The reusable transmitter unit 104 may be decoupled from the disposable base unit 102 before or after the disposable base unit 102 and sensor 132 are removed from the user. In block 616, the sensor of a new disposable base unit may be inserted into an interstitial fluid region of the user. In block 618, the new disposable base unit may be attached to the user. In block 620, the reusable transmitter unit may be coupled to the new disposable base unit so that the transmitter unit receives power from the new disposable base unit and is coupled to the sensor of the new disposable base unit. The reusable transmitter unit 104 may be attached to the new disposable base unit 102 before or after the sensor 132 is inserted into interstitial fluid region of the user. In block 622, the transmitter unit and sensor of the new disposable base unit may be employed to monitor analyte levels within the user for a second predetermined time period. For example, the transmitter unit 104 and new disposable base unit 102 may be employed for another 7, 10, 14 or other number of days. As mentioned, transmitter unit 104 may be used 10, 20, 50, 100 or more times (each time with a new disposable base unit).

Figure 7:
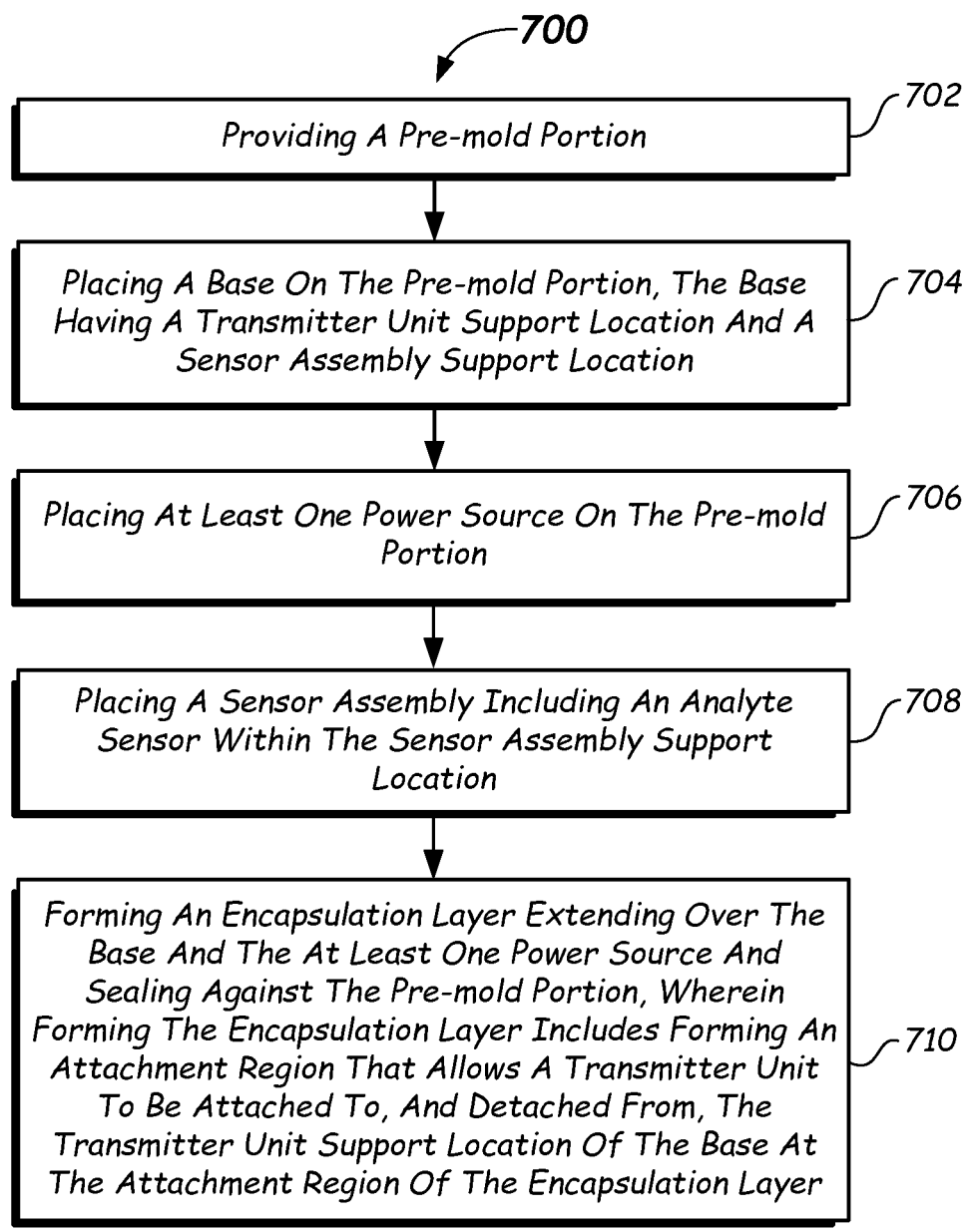
FIG. 7 illustrates a flowchart of an example method of forming a wearable device for use during continuous analyte monitoring in accordance with embodiments provided herein.

FIG. 7 is a flowchart of an example method 700 of forming a wearable device for use during continuous analyte monitoring provided herein. With reference to FIG. 7, in block 702, a pre-mold portion is provided (e.g., pre-mold encapsulation layer 142). For example, a liquid silicone rubber (LSR), thermoplastic elastomer (TPE), polyvinyl chloride (PVC), acrylonitrile butadiene styrene (ABS), polyoxymethylene (POM), polycarbonate, high durometer silicone, or another suitable material may be placed in a molding tool. The pre-mold portion 142 may be employed to secure or otherwise support components of the wearable device in their proper position prior to molding (e.g., over molding). In block 704, a base is placed on the pre-mold portion, the base having a transmitter unit support location and a sensor assembly support location. For example, base 106 may be placed on the pre-mold portion 142. In block 706, at least one power source is placed on the pre-mold portion. In some embodiments, power source 114a and/or 114b may be placed directly on the pre-mold portion 142, while in other embodiments, power source 114a and/or 114b may be placed on the power source support locations 108a and/or 108b of base 106. In some embodiments, in block 708, a sensor assembly including an analyte sensor may be placed within the sensor assembly support location. In other embodiments, a dummy insertion device shaped similar to the insertion device 124 may be placed within the sensor assembly support location (prior to molding) to protect the sensor and to ensure that the opening 140 for insertion device 124 is formed properly. When a dummy insertion device is employed, the dummy insertion device may be removed after molding and insertion device 124 may be placed within opening 140. Placement of the sensor assembly within the sensor assembly support location 112 may include placing connector 122 within the transmitter unit support location 110 and connecting connector 122 to sensor 132. Connector 122 may also be connected to power source 114a and/or 114b as described previously.

In block 710, an encapsulation layer is formed that extends over the base and the at least one power source and seals against the pre-mold portion. During encapsulation layer formation, an attachment region (e.g., opening 138, attachment region 154) is provided that allows a transmitter unit to be attached to and detached from the transmitter unit support location of the base at the attachment region of the encapsulation layer. This may be performed by using a dummy transmitter unit placed within the transmitter unit support location 110 of the base 106 prior to molding, for example.

In some embodiments, the encapsulation layer may be formed a temperature of less than 100° C., and in some embodiments less than 80° C. Example polymer materials for the encapsulation layer can include, for example, liquid silicone rubber (LSR), thermoplastic elastomer (TPE), or the like.

Figure 16:
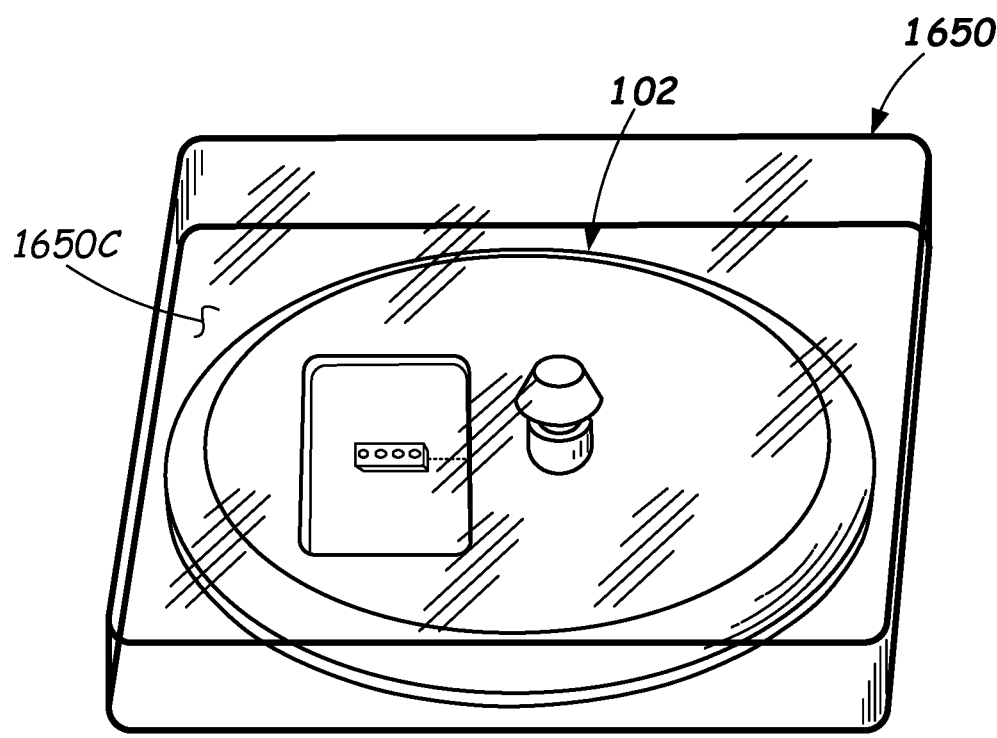
FIGS. 16 and 17 illustrate packaging of a continuous analyte monitoring wearable device in accordance with embodiments provided herein.
Figure 17:
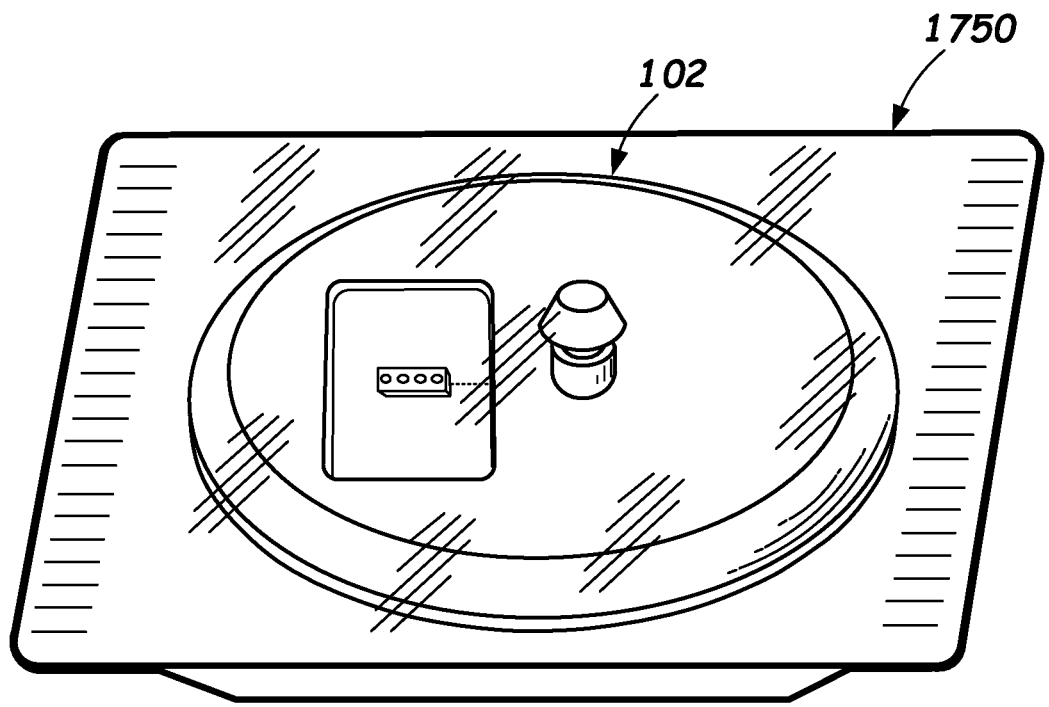

The encapsulation layer (e.g., encapsulation layer 136) forms a sealed disposable base unit (base unit 102) that may receive a transmitter unit 104 prior to use. Following formation of the encapsulation layer, an adhesive layer may be provided on the bottom of the pre-mold portion and used to secure the base unit 102 to a user during continuous analyte monitoring with the wearable device. Thereafter, the disposable base unit 102 including the insertion devoice and sensor assembly may be sterilized and packaged for use (e.g., separate from the transmitter unit 104). For example, e-beam sterilization or another sterilization method may be employed to sterilize the various components of the disposable base unit 102, such as the sensor 132, insertion device 124, insertion device cap 126, etc. Example packaging 1650 may include a plastic housing 1650H having a removable plastic or foil seal, or other sealing cover 1650C such as shown in FIG. 16 sealing the sterilized disposable base unit 102, although any suitable sterile packaging may be used. In another example, the sterilized disposable base unit 102 may be received and sealed in a laminated foil and plastic sheet 1750 enclosure as shown in FIG. 17. The wearable device may be employed by removing the sterilized base unit from its sterile packaging, inserting the reusable transmitter unit 104 into the base unit 102, removing an adhesive strip from the bottom of the base unit 102 and inserting the sensor 132 into a user while attaching the base unit 102 to the user's skin. Any suitable insertion device may be employed for inserting the sensor 132 into an interstitial fluid region of the user.

Figure 8:
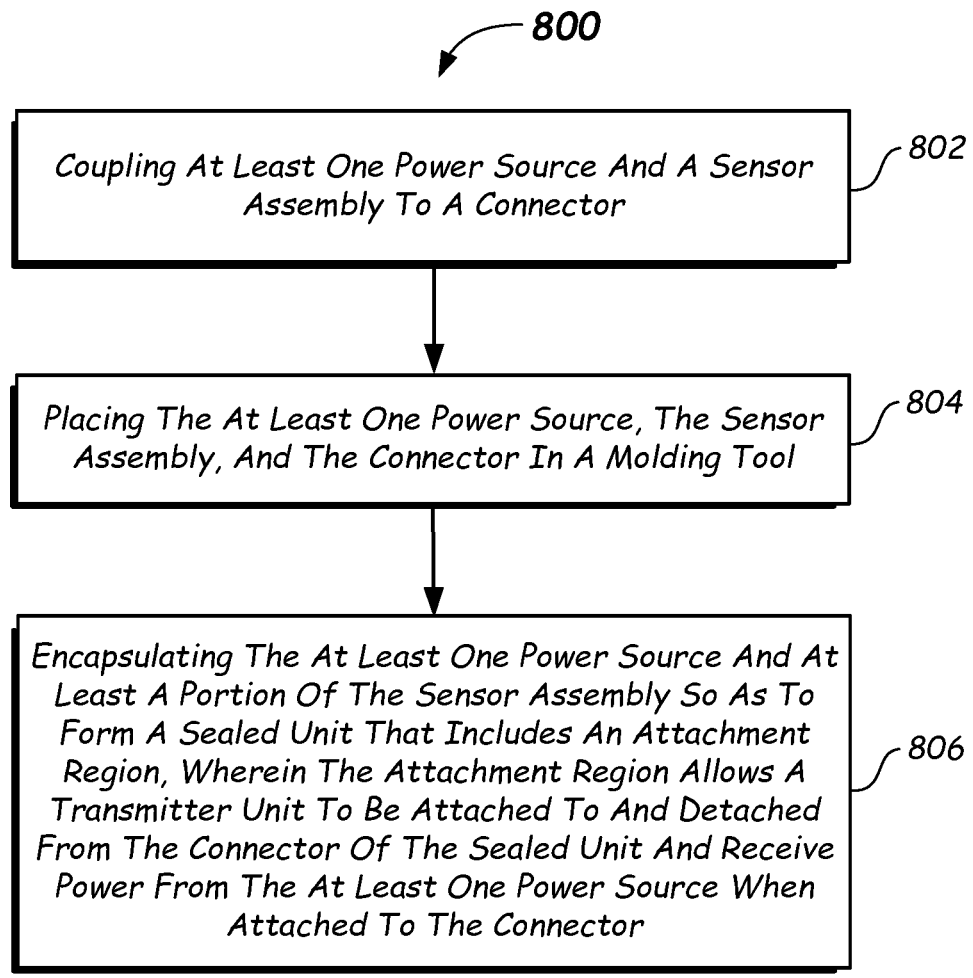
FIG. 8 is a flowchart of another example method of forming a wearable device for use during continuous analyte monitoring in accordance with embodiments provided herein.

FIG. 8 is a flowchart of another example method 800 of forming a wearable device for use during continuous analyte monitoring provided herein. With reference to FIG. 8, in block 802, at least one power source and a sensor assembly are coupled to a connector (e.g., power source 114a and/or 114b may be coupled to connector 122, as may be sensor 132). In block 804, the at least one power source, the sensor assembly, and the connector are placed in the molding tool. In some embodiments, a sensor assembly including an insertion device and an analyte sensor may be placed at the sensor assembly support location of the base 106. In other embodiments, a dummy insertion device shaped similar to the insertion device 124 may be placed within the sensor assembly support location (prior to molding) to ensure that the sensor 132 is protected and opening 140 for insertion device 124 is formed properly. When a dummy insertion device is employed, the dummy insertion device may be removed after molding and insertion device 124 may be placed within opening 140.

In block 806, the base, the at least one power source, and at least a portion of the sensor assembly are encapsulated using the molding tool to form a sealed unit. Such encapsulation includes forming an attachment region (e.g., 138) in the sealed unit that allows a transmitter unit 104 to be attached to and detached from the transmitter unit support location 110 of the base 106. This may be performed by using a dummy transmitter unit placed at the transmitter unit support location 110 of the base 106 during molding, for example.

In some embodiments, encapsulating the base 106 and the at least one power source 114a, 114b may be performed at a temperature of less than 100° C., and in some embodiments less than 80° C. Example materials for the encapsulating the base 106 and the at least one power source 114a, 114b include liquid silicone rubber (LSR), thermoplastic elastomer (TPE), or the like. Other suitable encapsulating materials may be used.

Encapsulating the base 106 and power source(s) 114a, 114b forms a sealed disposable base unit (e.g., base unit 102) that may receive a transmitter unit 104 prior to use. Following formation of the disposable base unit 102, an adhesive layer may be provided on the bottom of the base unit 102 and used to secure the base unit 102 to a user during continuous analyte monitoring with the wearable device. Thereafter, the disposable base unit may be sterilized and packaged for use (e.g., separate from the transmitter unit) as previously described.

Figure 9:
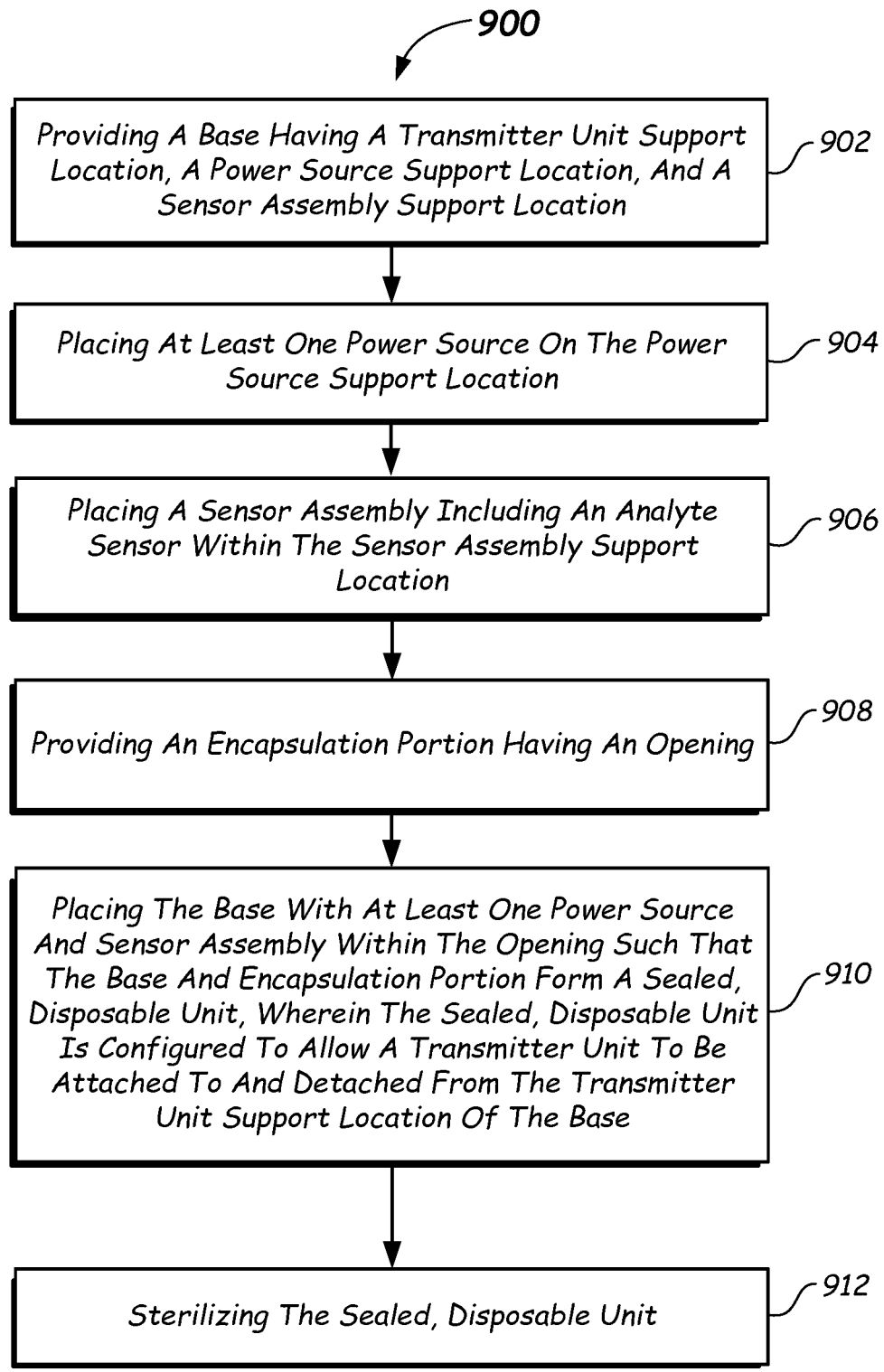
FIG. 9 is a flowchart of another example method of forming a wearable device for use during continuous analyte monitoring in accordance with embodiments provided herein.

FIG. 9 is a flowchart of another example method 900 of forming a wearable device for use during continuous analyte monitoring provided herein. With reference to FIG. 9, in block 902, a base (e.g., see base 106 of FIGS. 3A-3B) is provided having a transmitter unit support location (e.g., transmitter unit support location 110), a power source support location (e.g., power source support location 108a, 108b), and a sensor assembly support location (e.g., sensor assembly support location 112). In block 904, at least one power source (e.g., power source 114a, 114b) is placed at the power source support location (e.g., power source support location 108a, 108b) of the base (e.g., base 106). In block 906, a sensor assembly including an analyte sensor (e.g., analyte sensor 132) and/or an insertion device (e.g., insertion device 124) may be placed within the sensor assembly support location (e.g., sensor assembly support location 112). Placement of the sensor assembly within the sensor assembly support location 112 may include placing connector 122 within the transmitter unit support location 110 and connecting connector 122 to sensor 132. Connector 122 may also be connected to power source 114a and/or 114b as described herein.

In block 908, an encapsulation portion (e.g., encapsulation portion 136) is provided having an opening (e.g., opening 340) for the base 106. For example, a liquid silicone rubber (LSR), thermoplastic elastomer (TPE), thermosetting or thermoplastic polymer, or similar encapsulation portion 136 may be provided that includes an opening 440 formed therein, which allows the base 106 to be inserted into the opening 440 of the encapsulation portion 136. At least one power source (e.g., power sources 114a, 114b) and/or sensor assembly (e.g., 132) can be coupled to the base 106.

In block 910, the base (e.g., base 106 with the at least one power source 114a, 114b and sensor assembly 132 coupled thereto) is placed within the opening 340 of the encapsulation portion 136. In this embodiment, the base 106 can be sealed to the opening 340, and the edges of the base 106 can be sealed to the encapsulated portion 136 such that the base 106 and encapsulation portion 136 form a sealed, disposable unit. The sealed, disposable unit is configured to allow a transmitter unit 104 to be attached to and detached from the transmitter unit support location 110 of the base 106. In some embodiments, insertion device 124 and/or insertion device cap 126 may be coupled to the base unit 102 after the base is inserted into the pre-mold portion comprising the encapsulation portion 136.

Placing the base 106, sensor 132 and power source(s) 114a, 114b within the encapsulation portion 136 forms a sealed disposable base unit (base unit 102) that may receive a transmitter unit 104 prior to use. Following formation of the disposable base unit 102, an adhesive layer may be provided on the bottom of the base unit 102 and used to secure the base unit 102 to a user during continuous analyte monitoring with the wearable device 100. Thereafter, in block 912, the sealed, disposable unit (e.g., base unit 102) may be sterilized and packaged for use (e.g., separate from the transmitter unit), as previously described.

The wearable devices described herein may be used to monitor analyte concentration of any desired analyte. Example analytes that may be detected and/or monitored include glucose, cholesterol, lactate, uric acid, alcohol, or the like. In some embodiments, sensor 132 and/or sensor assembly 402 (e.g., microneedle array) may be continuously operated at a constant potential against a reference electrode, such as an Ag/AgCl electrode, or a combined reference-counter electrode. Sensor 132 and/or sensor assembly 402 may also be operated with two working electrodes where one is dedicated to measuring a point-of-interest analyte, such as glucose, by a glucose specific enzyme such as glucose oxidase. The other electrode is dedicated to measuring the background signals that result from interference species such as uric acid, acetaminophen or the like. In this dual electrode operation scheme, the interference signal may be constantly subtracted from the main signal of the point-of-interest analyte by either simple subtraction or another algorithmic method.

Figure 10A:
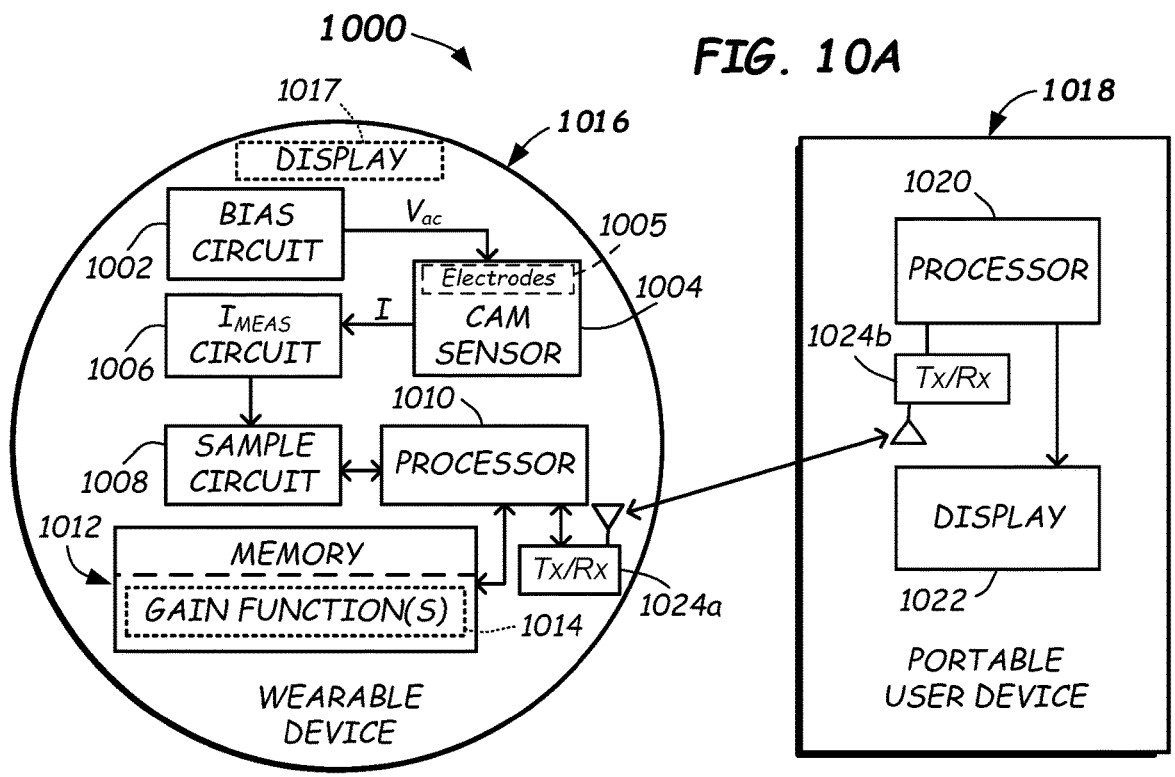
FIG. 10A illustrates a high-level block diagram of an example CGM system in accordance with embodiments provided herein.

FIG. 10A illustrates a high-level block diagram of an example continuous analyte monitoring (CAM) device 1000 in accordance with embodiments provided herein. Although not shown in FIG. 10A, it is to be understood that the various electronic components and/or circuits are configured to couple to a power source, such as but not limited to, a battery. CAM device 1000 includes a bias circuit 1002 that may be configured to couple to a CAM sensor 1004. Bias circuit 1002 may be configured to apply a bias voltage, such as a continuous DC bias, to an analyte-containing fluid through CAM sensor 1004. In this example embodiment, the analyte-containing fluid may be human interstitial fluid, and the bias voltage may be applied to one or more electrodes 1005 of CGM sensor 1004 (e.g., a working electrode, a background electrode, etc.).

In some embodiments, the CAM sensor 1004 may include two electrodes and the bias voltage may be applied across the pair of electrodes. In such cases, current may be measured through the CAM sensor 1004. In other embodiments, the CAM sensor 1004 may include three electrodes such as a working electrode, a counter electrode, and a reference electrode. In such cases, the bias voltage may be applied between the working electrode and the reference electrode, and current may be measured through the working electrode, for example. The CAM sensor 1004 can include chemicals which react with the analyte (e.g., glucose) in a reduction-oxidation reaction, which affects the concentration of charge carriers and the time-dependent impedance of the CAM sensor 1004. Example chemicals for glucose reaction include glucose oxidase, glucose dehydrogenase, or the like. In some embodiments, a mediator such as ferricyanide or ferrocene for glucose reaction may be employed. In some embodiments, CAM sensor 1004 may include a microneedle or a sensor assembly including a plurality of microneedles, such as a microneedle array.

The bias voltage generated and/or applied by bias circuit 1002 may range from about 0.1 to 1 volts versus the reference electrode, for example. Other bias voltages may be used.

A current through CAM sensor 1004 in an analyte-containing fluid responsive to the bias voltage may be conveyed from CAM sensor 1004 to a current measurement ($I_{meas}$) circuit 1006 (also referred to as current sensing circuitry). Current measurement circuit 1006 may be configured to sense and/or record a current measurement signal that has a magnitude indicative of the magnitude of the current conveyed from CAM sensor 1004 (e.g., using a suitable current-to-voltage converter (CVC), for example). In some embodiments, current measurement circuit 1006 may include a resistor having a known nominal value and a known nominal precision (e.g., 0.1% to 5%, or even smaller than 0.1%, in some embodiments), through which the current conveyed from CAM sensor 1004 is passed. A voltage developed across the resistor of current measurement circuit 1006 represents the magnitude of the current, and may be referred to as the current measurement signal (or raw analyte (e.g., glucose) signal $Signal_{Raw}$).

In some embodiments, a sample circuit 1008 may be coupled to current measurement circuit 1006, and may be configured to sample the current measurement signal, and may produce digitized time-domain sample data that is representative of the current measurement signal (e.g., digitized glucose signals). For example, sample circuit 1008 may be any suitable A/D converter circuit configured to receive the current measurement signal, which is an analog signal, and convert it to a digital signal having a desired number of bits as an output. The number of bits output by sample circuit 1008 may be sixteen in some embodiments, but more or fewer bits may be used in other embodiments. In some embodiments, sample circuit 1008 may sample the current measurement signal at a sampling rate in the range of about 10 samples per second to 1000 samples per second. Faster or slower sampling rates may be used. For example, sampling rates such as about 10 kHz to 100 kHz may be used and down-sampled to further reduce signal-to-noise ratio. Any suitable sampling circuitry may be employed.

Still referring to FIG. 10A, a processor 1010 may be coupled to sample circuit 1008, and may be further coupled to a memory 1012. In some embodiments, processor 1010 and sample circuit 1008 are configured to directly communicate with each other via a wired pathway (e.g., via a serial or parallel connection). In other embodiments, the coupling of processor 1010 and sample circuit 1008 may be by way of memory 1012. In this arrangement, sample circuit 1008 writes digital data to memory 1012, and processor 1010 reads the digital data from memory 1012.

Memory 1012 may have stored therein one or more gain functions 1014 for using in determining glucose values based on raw glucose signals (from current measurement circuit 1006 and/or sample circuit 1008). For example, in some embodiments, three or more gain functions may be stored in memory 1012, each for use with different segments (time periods) of CAM collected data. Memory 1012 also may have stored therein a plurality of instructions. In various embodiments, processor 1010 may be a computational resource such as but not limited to a microprocessor, a microcontroller, an embedded microcontroller, a digital signal processor (DSP), a field programmable gate array (FPGA) configured to perform as a microcontroller, or the like.

In some embodiments, the plurality of instructions stored in memory 1012 may include instructions that, when executed by the processor 1010, cause the processor 1010 to (a) cause the CAM device 1000 (via bias circuit 1002, CAM sensor 1004, current measurement circuit 1006 and/or sample circuit 1008) to measure analyte signals (e.g., current signals) from interstitial fluid; (b) store analyte signals in memory 1012; (c) compute analyte values (e.g., concentrations) based on measured and/or stored analyte signals; and (e) communicate the analyte values to a user.

Memory 1012 may be any suitable type of memory, such as but not limited to, one or more of a volatile memory and/or a non-volatile memory. Volatile memory may include, but is not limited to a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. Memory 1012 may be packaged as a single chip or as multiple chips, for example. In some embodiments, memory 1012 may be embedded, with one or more other circuits, in an integrated circuit, such as, for example, an application specific integrated circuit (ASIC).

As noted above, memory 1012 may have a plurality of instructions stored therein that, when executed by processor 1010, cause processor 1010 to perform various actions specified by one or more of the stored plurality of instructions. Memory 1012 may further have portions reserved for one or more "scratchpad" storage regions that may be used for read or write operations by processor 1010 responsive to execution of one or more instructions of the plurality of instructions.

In the embodiment of FIG. 10A, bias circuit 1002, CAM sensor 1004, current measurement circuit 1006, sample circuit 1008, processor 1010, and memory 1012, may be disposed within a wearable sensor portion 1016 of CAM device 1000 (e.g., wearable device 100 or 400 described above). In some embodiments, wearable sensor portion 1016 may include a display 1017 for displaying information such as analyte concentration information (e.g., without use of external equipment). Display 1017 may be any suitable type of human-perceivable display, such as but not limited to, a liquid crystal display (LCD), a light-emitting diode (LED) display, an organic light emitting diode (OLED) display, or the like.

In some embodiments, all electronic circuitry within CAM device 1000 may be contained within a reusable transmitter unit (e.g., reusable transmitter unit 104) as described herein, such as bias circuit 1002, current measurement circuit 1006, sample circuit 1008, processor 1010, memory 1012, transmitter/receiver circuit 1024a and/or display 1017. CAM sensor 1004 and any power source may be located within a disposable base unit (e.g., disposable base unit 102).

Still referring to FIG. 10A, CAM device 1000 may further include a portable user device portion 1018. A processor 1020 and a display 1022 may be disposed within portable user device portion 1018. Display 1022 may be coupled to processor 1020. Processor 1020 may control the text or images shown by display 1022. Wearable sensor portion 1016, and portable user device portion 1018, may be communicatively coupled. In some embodiments the communicative coupling of wearable sensor portion 1016, and portable user device portion 1018, may be by way of wireless communication via transmitter circuitry and/or receiver circuitry, such as transmit/receive circuit TxRx 1024a in wearable sensor portion 1016 and transmit/receive circuit TxRx 1024b in portable user device 1018, for example. Such wireless communication may be by any suitable means including but not limited to standards-based communications protocols such as the Bluetooth® communications protocol. In various embodiments, wireless communication between wearable sensor portion 1016 and portable user device portion 1018 may alternatively be by way of near-field communication (NFC), radio frequency (RF) communication, infra-red (IR) communication, or optical communication. In some embodiments, wearable sensor portion 1016 and portable user device portion 1018 may be connected by one or more wires.

Display 1022 may be any suitable type of human-perceivable display, such as but not limited to, a liquid crystal display (LCD), a light-emitting diode (LED) display, an organic light emitting diode (OLED) display, or the like.

Figure 10B:
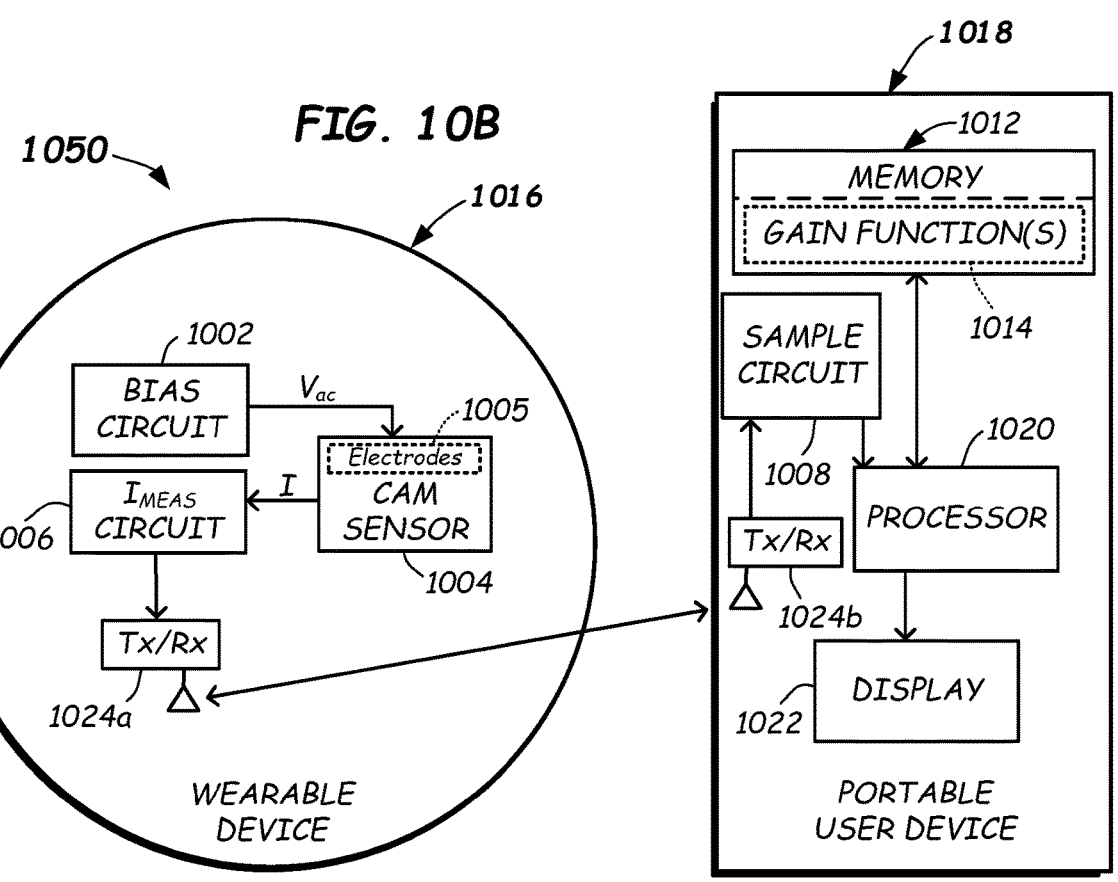
FIG. 10B illustrates an example CGM system that is similar to the embodiment illustrated in FIG. 10A, but having a different partitioning of components in accordance with embodiments provided herein.

Referring now to FIG. 10B, an example CAM device 1050 is shown that is similar to the embodiment illustrated in FIG. 10A, but having a different partitioning of components. In CAM device 1050, the wearable sensor portion 1016 includes the bias circuit 1002 coupled to the CAM sensor 1004, and the current measurement circuit 1006 coupled to the CAM sensor 1004. The portable user device portion 1018 of CAM device 1050 includes the sample circuit 1008 coupled to processor 1020, and the display 1022 coupled to processor 1020. Processor 1020 is further coupled to memory 1012 that has the gain function(s) 1014 stored therein. In some embodiments, processor 1020 in CAM device 1050 may also perform the previously-described functions performed by processor 1010 of CAM device 1000 of FIG. 10A, for example. Wearable sensor portion 1016 of CAM device 1050 may be smaller and lighter, and therefore less invasive, than CAM device 1000 of FIG. 10A because sample circuit 1008, processor 1010, memory 1012, etc., are not included therein. Other component configurations may be employed. For example, as a variation to the CAM device 1050 of FIG. 10B, sample circuit 1008 may remain on wearable sensor portion 1016 (such that portable user device 1018 receive digitize analyte (e.g., glucose) signals from wearable sensor portion 1016).

Figure 11:
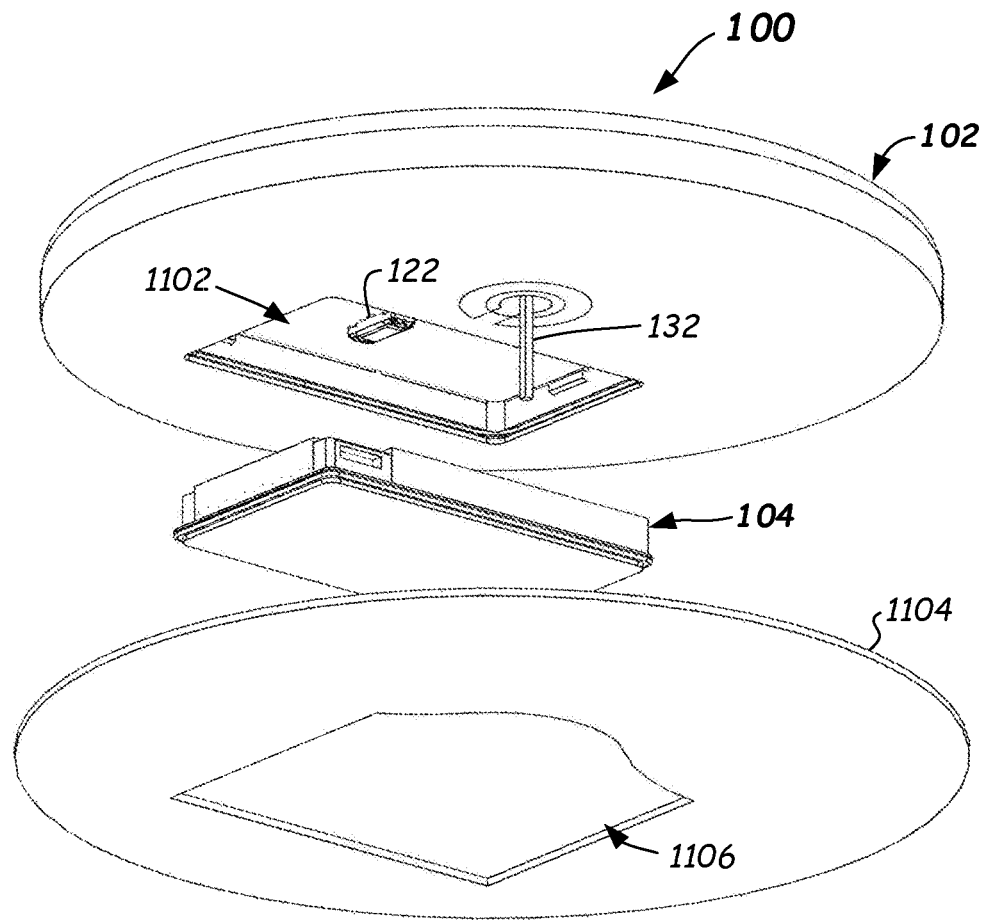
FIG. 11 is an exploded bottom view of a wearable device wherein the base unit has an opening that allows a transmitter unit to be inserted in or removed from base unit in accordance with some embodiments provided herein.

While in some embodiments, the transmitter unit 104 is shown as being removable and/or insertable into a top surface of the base unit 102, it will be understood that in other embodiments, transmitter unit 104 may be removable and/or insertable into other surfaces of the base unit 102. For example, FIG. 11 illustrates a bottom perspective view of a base unit 102 having an opening 1102 that allows transmitter unit 104 to be inserted in or removed from base unit 102 in accordance with some embodiments and as described above. Transmitter unit 104 may receive electrical power and analyte signals (e.g., analyte current signals) from base unit 102 in some embodiments. An adhesive layer 1104 may be provided on the bottom of base unit 102 for allowing the wearable device 100 formed by base unit 102 and transmitter unit 104 to be secured to the skin of a user. An opening 1106 in adhesive layer 1104 allows transmitter unit 104 to be inserted into and removed from base unit 102.

Figure 12A:
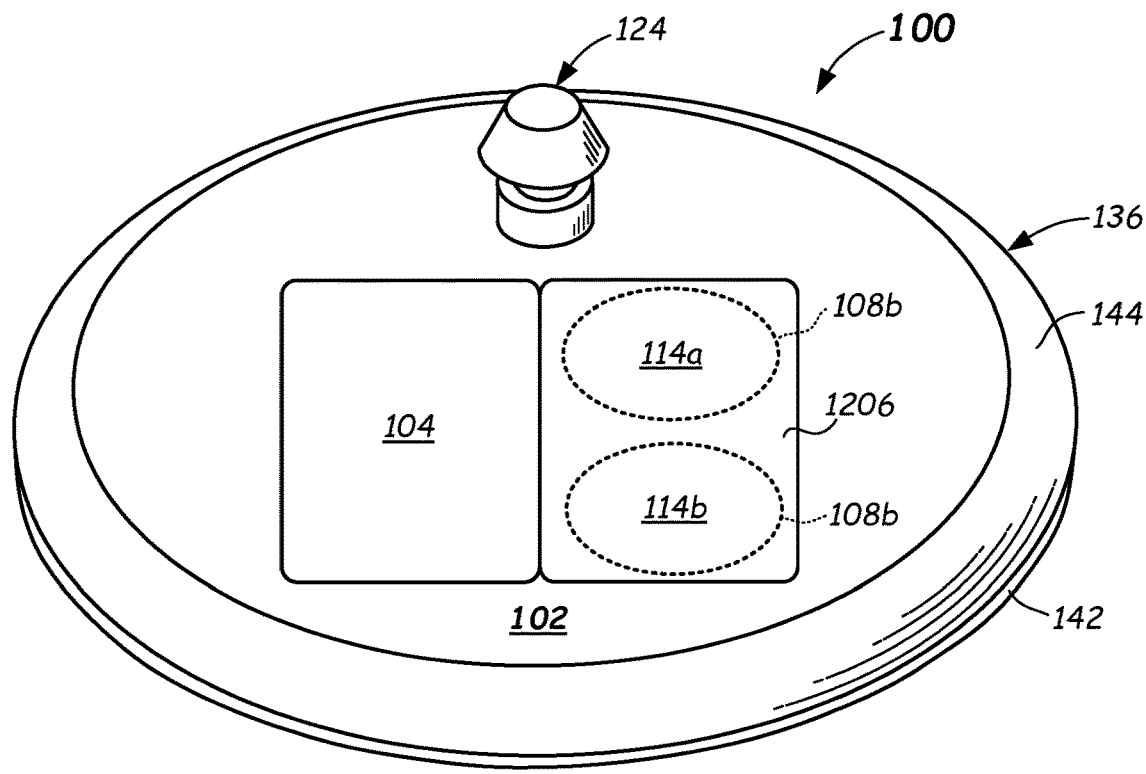
FIG. 12A illustrates a top perspective view of another wearable device for use during continuous analyte monitoring in accordance with embodiments provided herein.
Figure 12B:
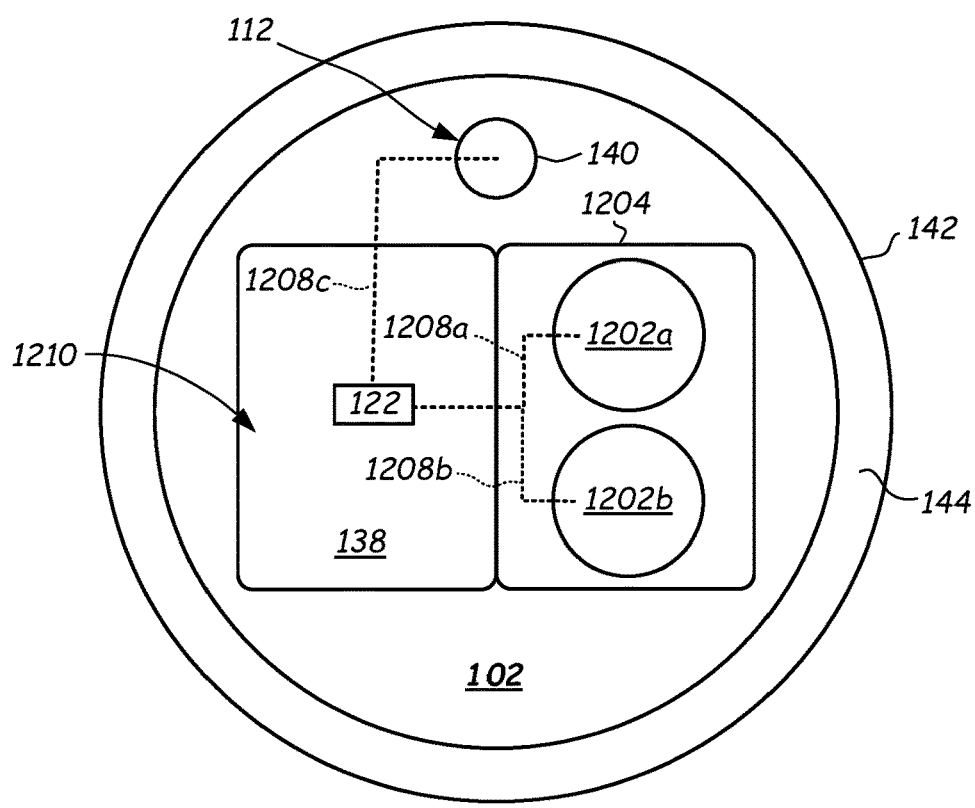
FIG. 12B is a top view of a base unit of FIG. 12A without an insertion device, a transmitter unit or power sources in accordance with embodiments provided herein.
Figure 12C:
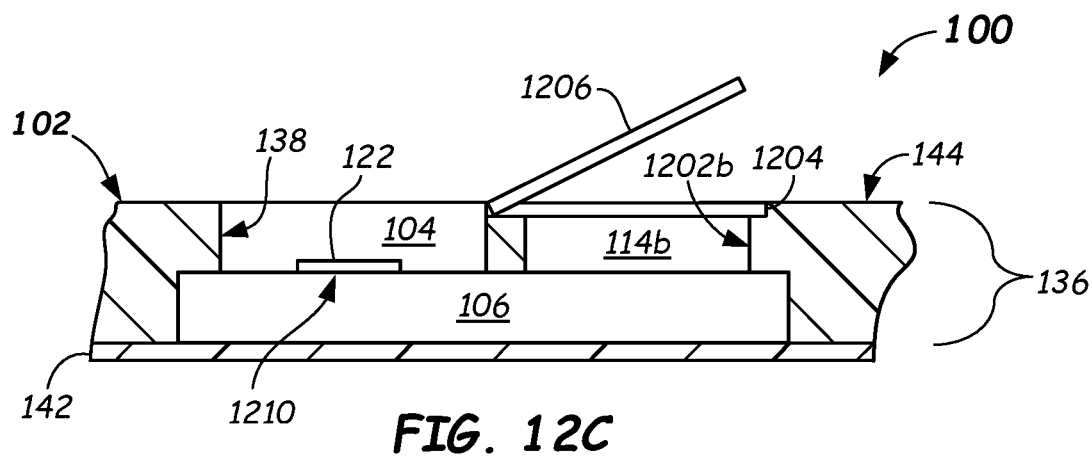
FIG. 12C is a cross-sectioned side view of a portion of the wearable device of FIG. 12A in accordance with embodiments provided herein.

FIG. 12A illustrates a top perspective view of another embodiment of wearable device 100 for use during continuous analyte monitoring in accordance with embodiments provided herein. FIG. 12B is a top view of base unit 102 of FIG. 12A without the insertion device 124, transmitter unit 104, or power sources 114a and 114b installed in accordance with embodiments provided herein. FIG. 12C is a perspective side view of a wearable device 100 of FIG. 12A in accordance with embodiments provided herein.

With reference to FIGS. 12A and 12B, wearable device 100 may be formed by placing base 106 (not separately shown) on pre-mold encapsulation layer 142 and forming top encapsulation layer 144 over base 106. As shown in FIG. 12B, during formation of top encapsulation layer 144, such as by molding, opening 138 is formed for transmitter unit 104, opening 140 is formed for insertion device 124, openings 1202a and 1202b are formed for power sources 114a and 114b, respectively, and a recess 1204 is formed for a cover 1206 for power sources 114a and 114b (see FIG. 12C). In some embodiments, cover 1206 may be coupled to and/or a part of transmitter unit 104 and snap, pivot, and/or hinge into recess 1204 when transmitter unit 104 is placed within opening 138 of disposable base unit 102. In other embodiments, cover 1206 may be separate from transmitter 104. Cover 1206 may form part of encapsulation layer 136 when it is positioned to cover power sources 114a and 114b (e.g., along with pre-mold encapsulation layer 142 and top encapsulation layer 144). Cover 1206 may be formed from liquid silicone rubber (LSR), thermoplastic elastomer (TPE), polyvinyl chloride (PVC), acrylonitrile butadiene styrene (ABS), polyoxymethylene (POM), polycarbonate, high durometer silicone, or another suitable material, for example.

After formation of base unit 102 with opening 138, opening 140, openings 1202a and 1202b, and recess 1204, power sources 114a and 114b may be installed in openings 1202a and 1202b and insertion device 124 may be installed in opening 140. Base unit 102 then may be sterilized, such as by using e-beam sterilization, for use with transmitter unit 104 during continuous analyte monitoring as previously described. A dummy transmitter unit, insertion device 124, power sources 114a and 114b and/or cover 1206 may be employed, such as being provided as mold inserts or the like, during formation of top encapsulation layer 144 so that openings 138, 140, 1202a and 1202b, and recess 1204 are formed.

In some embodiments, openings 1202a and 1202b may include electrical connections 1208a, 1208b that couple power sources 114a and 114b to connector 122 provided in opening 138 for supplying electrical power to any transmitter unit 104 inserted in opening 138. Connector 122 may also include electrical connection 1208c configured to couple to an analyte sensor to be inserted by insertion device 124 during use of wearable device 100 as previously described.

Figure 13A:
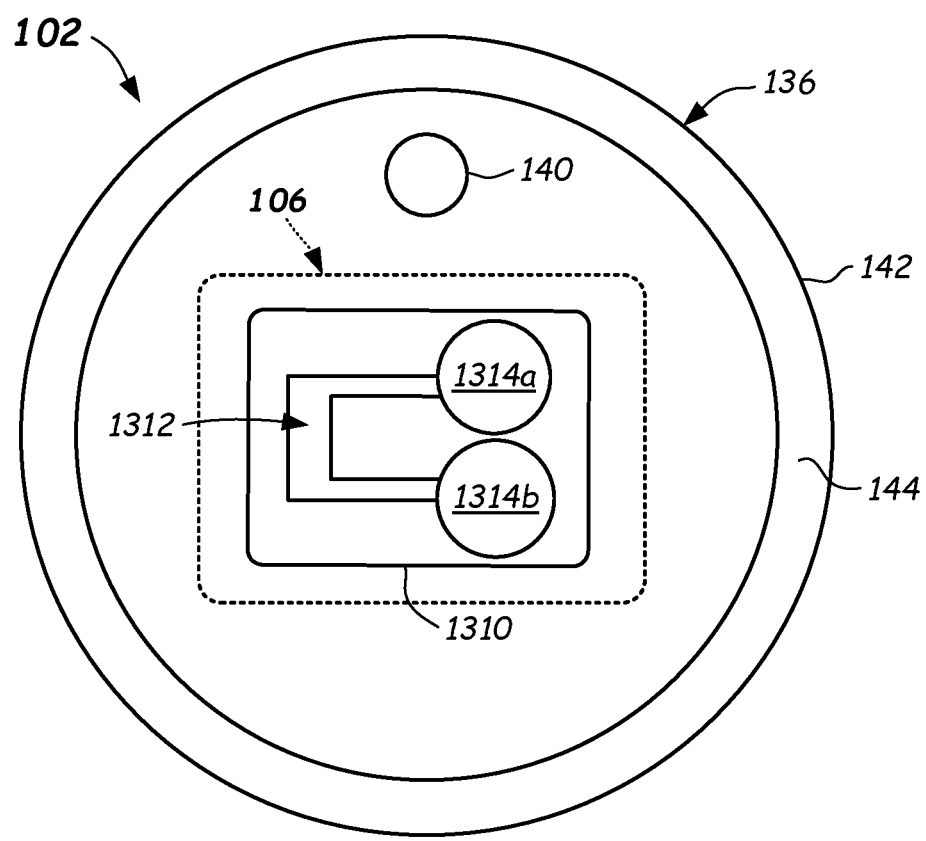
FIGS. 13A and 13B are top views of another example of disposable base unit in accordance with embodiments provided herein.
Figure 13B:
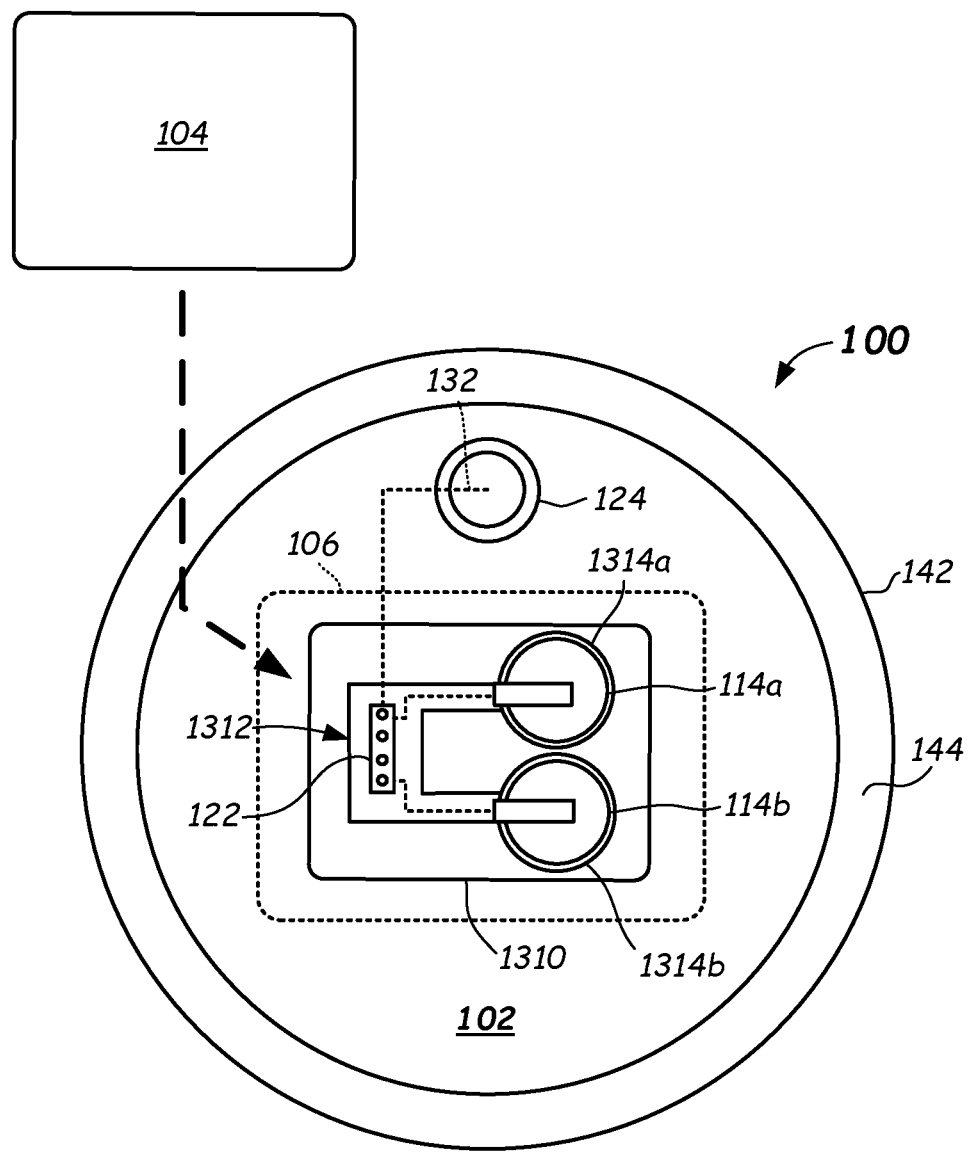

FIGS. 13A and 13B are top views of another example of disposable base unit 102 in accordance with embodiments provided herein. With reference to FIG. 13A, the disposable base unit 102 includes an attachment region 1310 configured to allow transmitter unit 104 to be coupled to disposable base unit 102 (for receiving power and for connecting to an analyte sensor), and also decoupled therefrom, as previously described. Attachment region 1310 includes a connector location 1312 at which connector 122 (FIG. 13B) may be located, and power source locations 1314a, 1314b at which one or more power sources, such as one or more batteries, may be located. Connector 122 (FIG. 13B) and power sources 114a, 114b may be positioned at connector location 1312 and power source locations 1214a, 1214b, respectively, as shown in FIG. 13B. When transmitter unit 104 is positioned at attachment region 1310, it may form a waterproof seal with base unit 102 so that connector 122 and power sources 114a, 114b are hermetically sealed and/or encapsulated.

With reference to FIGS. 13A and 13B, wearable device 100 (FIG. 13B) may be formed by providing a pre-mold encapsulation layer 142 and forming top encapsulation layer 144 having connector location 1312 and power source regions 1314a, 1314b formed therein (as well as attachment location 1310, such as an opening or recess). As shown in FIG. 13A, during formation of top encapsulation layer 144, attachment region 1310 is formed for transmitter unit 104, opening 140 is formed for receiving insertion device 124, connector location 1310 is formed for connector 122, and openings 1314a and 1314b are formed for receiving power sources 114a and 114b.

After formation of base unit 102 with attachment region 1310, connector location 1312, opening 140, and power source locations 1314a and 1314b, connector 122 may be placed in connector location 1312, power sources 114a and 114b may be installed in power source locations 1314a and 1314b and insertion device 124 may be installed in opening 140. Power sources 114a, 114b may be coupled to connector 122, along with an analyte sensor (e.g., sensor 132 shown dotted) that extends to opening 140 and couples with insertion device 124.

Base unit 102 then may be sterilized for use with transmitter unit 104 during continuous analyte monitoring, as previously described. Die plugs or inserts or dummy transmitter unit, insertion device, power sources and/or inserter may be employed during formation (e.g., molding) of top encapsulation layer 144 so that attachment location 1310, connector location 1312, opening 140, and power source locations 1314a and 1314b are appropriately formed.

Figure 14:
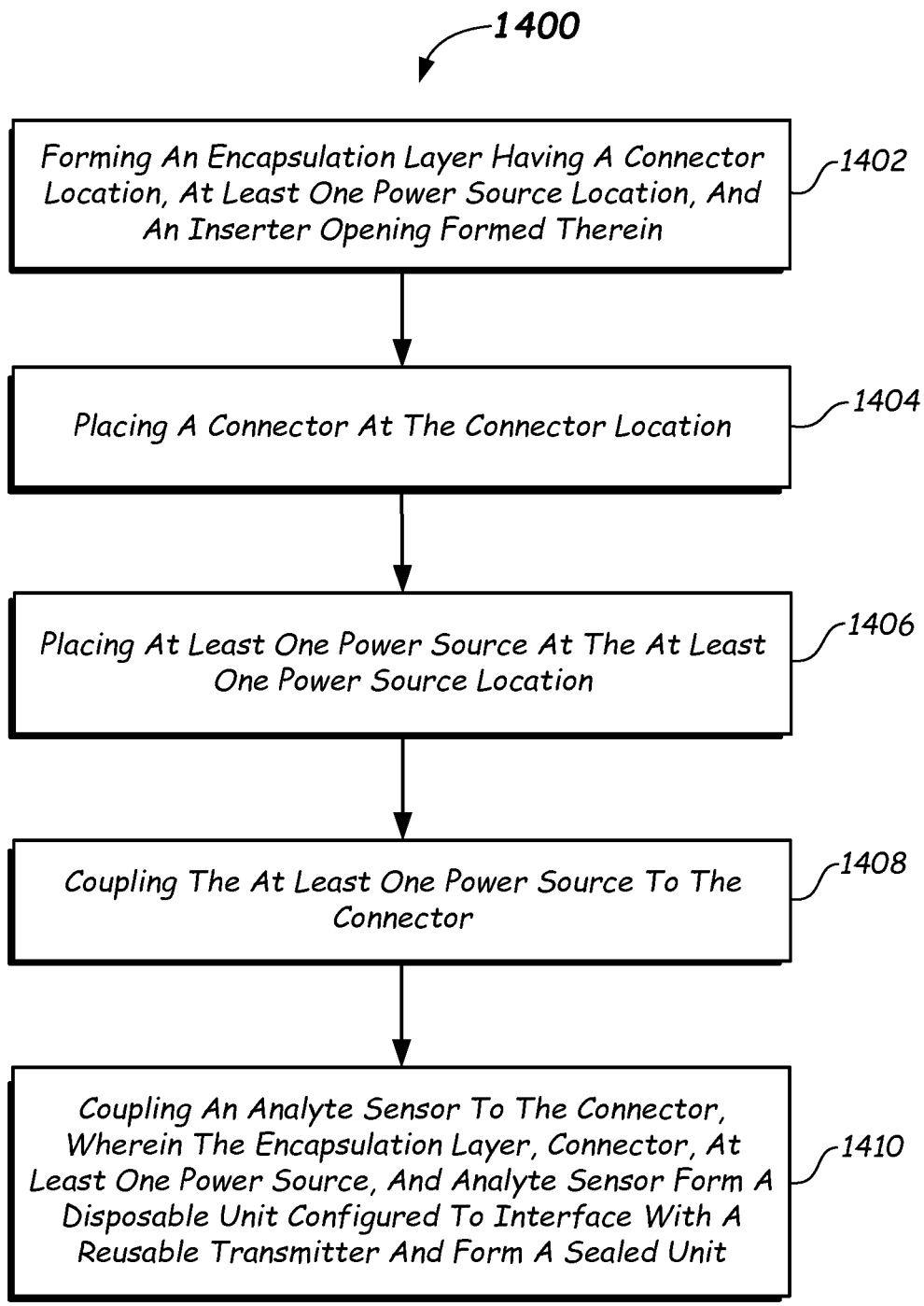
FIG. 14 illustrates a flowchart of a method of forming a wearable device for use during continuous analyte monitoring in accordance with embodiments provided herein.

In some embodiments, as shown in the flowchart of FIG. 14, a method 1400 of forming a wearable device (e.g., wearable device 100) adapted to use in continuous analyte monitoring includes, in block 1402, forming an encapsulation layer (e.g., encapsulation layer 136) having a connector location, at least one power source location, and an inserter opening formed therein (e.g., connector location 1312, power source locations 1314a, 1314b, and opening 140). The method 1400 further includes, in block 1404, placing a connector (e.g., connector 122) at the connector location, and, in block 1406, placing at least one power source (e.g., power sources 114a and/or 114b); at the at least one power source location (e.g., power source locations 1314a, 1314b). The placing of the connector 122 can be by any suitable method to achieve the electrical connections to the at least one power source (e.g., power sources 114a and/or 114b), and may include pin connectors and/or solder connections. In block 1408, the method 1400 includes coupling the at least one power source (e.g., power sources 114a and/or 114b) to the connector (e.g., connector 122), such as through electrical connections between the connector 122 and the at least one power source (e.g., power sources 114a and/or 114b. The method 1400 includes, in block 1410, coupling an analyte sensor (e.g., sensor 132 shown dotted) to the connector (e.g., connector 122). The coupling of the connector 122 can be by any suitable method to achieve the electrical connections between the connector 122 and the analyte sensor (e.g., sensor 132 shown dotted) and may include pin connectors and/or solder connections. The encapsulation layer (e.g., encapsulation layer 136), connector (e.g., connector 122), at least one power source (e.g., power source locations 114a, 114b), and analyte sensor (e.g., sensor 132) form a disposable unit configured to interface with a reusable transmitter unit (e.g., reusable transmitter unit 104) and form a sealed unit (e.g., a sealed unit of base unit 102 and reusable transmitter unit 104 of FIG. 13B, for example).

Figure 15:
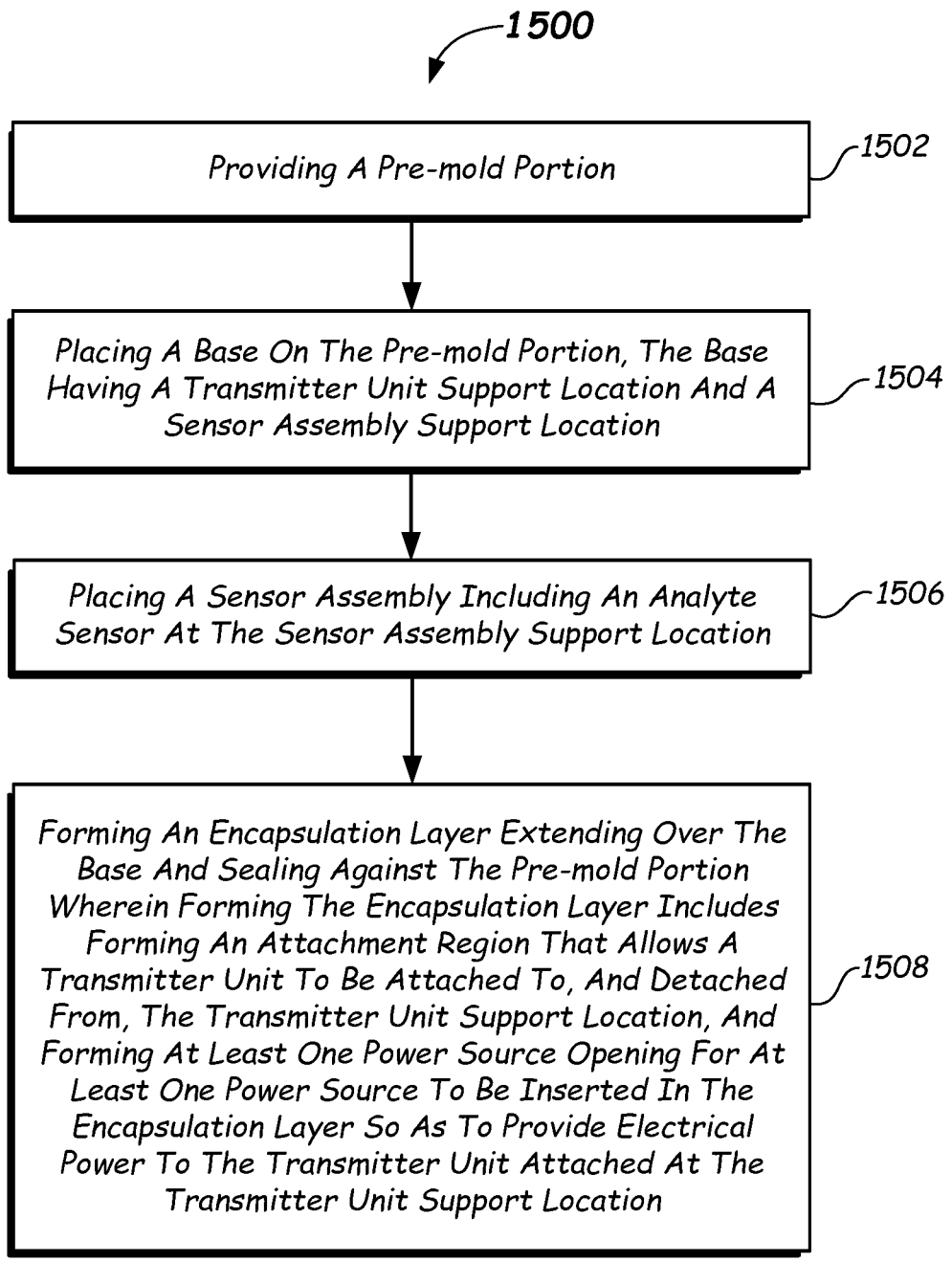
FIG. 15 illustrates a flowchart of another method of forming a wearable device for use during continuous analyte monitoring in accordance with embodiments provided herein.

In some embodiments, a method 1500 of forming a wearable device (e.g., wearable device 100 of FIGS. 12A-12C) that is configured to use in continuous analyte monitoring is provided, as is shown in the flowchart of FIG. 15, for example. The method 1500 includes, in block 1502, providing a pre-mold portion (e.g., a pre-mold encapsulation layer 142); in block 1504, placing a base (e.g., base 106) on the pre-mold portion, the base having a transmitter unit support location (e.g., transmitter unit support location 1210) and a sensor assembly support location (e.g., sensor assembly support location 112); and in block 1506, placing a sensor assembly including an analyte sensor (e.g., sensor 132) at the sensor assembly support location (e.g., sensor support location 112); and in block 1508 forming an encapsulation layer (e.g., encapsulation layer 144) extending over the base (e.g., base 106), and sealing against the pre-mold portion (pre-mold encapsulation layer 142).

Forming the top encapsulation layer 144 may include forming an attachment region (e.g., opening 138 or region 154) that allows a transmitter unit (e.g., transmitter unit 104 of FIG. 12A) to be attached to, and detached from, the transmitter unit support location 1210 of the base 106, such as attached to, and detached from, the transmitter unit support location 1210 (and connector 122). Forming the top encapsulation layer 144 may also include forming at least one power source opening (e.g., opening 1202*a* and/or 1202*b*) for at least one power source (e.g., to be inserted in the top encapsulation layer 144 so as to provide electrical power to the transmitter unit 104 attached at the transmitter unit support location 1210. The method 1500 may also include forming a connector (e.g., connector 122) within the transmitter unit support location 1210, and coupling an analyte sensor (e.g., analyte sensor 132) to the connector (e.g., connector 122). The encapsulation layer, connector, at least one power source 114*a*, 114*b*, and analyte sensor 132 form a disposable unit 102 configured to interface with a reusable transmitter unit the transmitter unit and form a sealed wearable device 100.

In some embodiments, a wearable device for use during continuous analyte monitoring is formed at a temperature of less than 100° C., and in some embodiments less than 80° C. The wearable device may include a disposable base unit having a power source and a reusable transmitter unit having electronics for the wearable device. The transmitter unit may have no separate power source, receiving electrical power solely from the disposable base unit to which it is coupled.

In some embodiments, a thumbnail groove, tab, or other grasping or prying feature may be provided on the transmitter unit 104 and/or base unit 102 to facilitate removal of the transmitter unit 104.

In one or more embodiments, a wearable device (e.g., wearable device 100 or 400) for continuous analyte monitoring may include a disposable base unit (e.g., base unit 102) that interfaces with a reusable transmitter unit (e.g., transmitter unit 104). The disposable base unit may include a power source and an analyte sensor, and may be configured to receive the reusable transmitter unit. The reusable transmitter unit may include all electronic circuitry for biasing the analyte sensor, measuring current through the analyte sensor, computing analyte values based on measured current through the analyte sensor, and communicating analyte values to a user (directly or via an external device). The disposable base unit may be configured to receive the reusable transmitter unit and supply electrical power to the electronic circuitry of the reusable transmitter unit. The disposable base unit may be sterilized and packaged separately from the reusable transmitter unit.

A sensor assembly may include one or more of a sensor, electrical leads that extend from the sensor, and/or an insertion device employed to insert the sensor (e.g., a sensor, a sensor and electrical leads, a sensor and an insertion device, a sensor, electrical leads and an insertion device, etc.).

Figure 18:
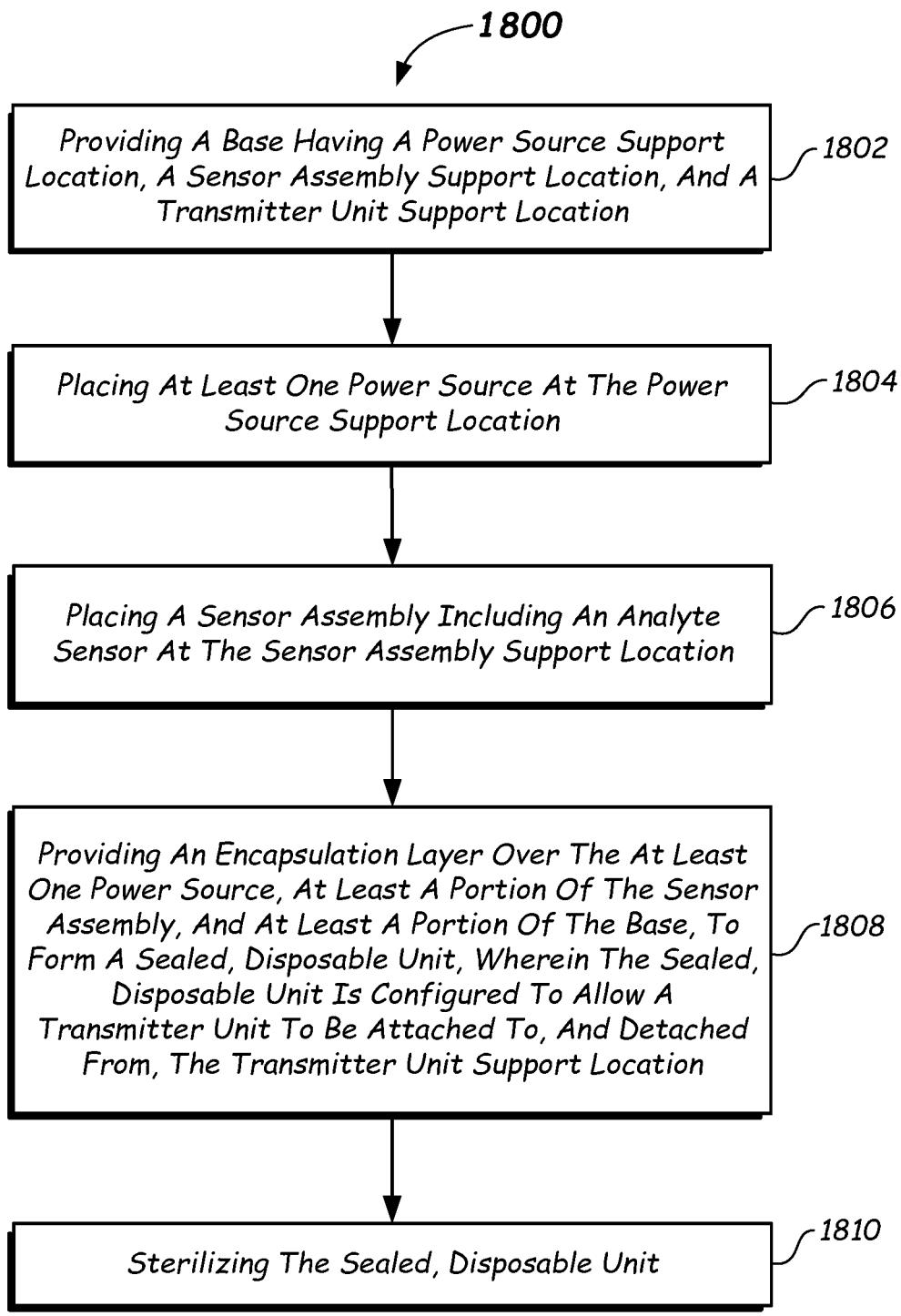
FIG. 18 illustrates a method of forming a continuous analyte monitoring wearable device in accordance with embodiments provided herein.

According to the disclosure, and as best shown in FIG. 18, a method of forming a continuous analyte monitoring wearable device is provided. The method 1800 includes, in block 1802, providing a base having a power source support location, a sensor assembly support location, and a transmitter unit support location, and in block 1804, placing at least one power source at the power source support location. The method 1800, further includes, in block 1806, placing a sensor assembly including an analyte sensor at the sensor assembly support location, and in block 1808, the method 1800 includes providing an encapsulation layer over the at least one power source, at least a portion of the sensor assembly, and at least a portion of the base, to form a sealed, disposable unit, wherein the sealed, disposable unit is configured to allow a transmitter unit to be attached to, and detached from, the transmitter unit support location. Finally, the method 1800 includes in block 1810 and sterilizing the sealed, disposable unit. Sterilization can be accomplished as is disclosed herein.

Embodiments provided herein allow for flexible and ultra-low profile continuous analyte monitoring systems. In some embodiments, the height of the system may be less than about 2.5 mm. This reduction in overall height may reduce interfere with clothing, be more discreet, and may improve overall wear comfort of the system. The flexible construction and components allow the sensor system to be contoured to a user's body through a range of motions and serves to increase overall user comfort. Critical components can be supported by rigid stiffeners in specific locations while maintaining overall flexibility. The power source(s) employed may be formed from a thin, bendable material, such as multiple batteries arranged in parallel.

In some embodiments, the materials used (e.g., LSR), flexible circuit boards, etc., provide a device that may be worn comfortably under clothing, has a low profile and avoid impacts, presents a soft flexible feel and appearance, and contours and moves with the dynamics of tissue flex, expansion and contraction. The disclosed devices also may protect sensor sites and internal hardware from fluid ingress and other use hazards, are applied easily and comfortably, provide breathability/air flow at skin adhesive areas and create a generally more user-friendly experience.

A flexible circuit board may be employed to support electronic components, such as an analog front end circuit and a transmitter module. The flexible circuit board may be fabricated from materials such copper, kapton, polyester (PET), polyethylene naphthalate (PEN), polymides, fiberglass and acrylic adhesives. The flexible circuit board may include electronic components in the form of a printed circuit and electronic components.

Example power sources include flexible lithium polymer batteries, coin cell batteries such as Lithium Manganese, Silver Oxide, and Alkaline coin batteries (e.g., CR 2032, SR516, and LR60 type coin batteries), or the like. Other circuit board and/or power source types may be used.

The foregoing description discloses only example embodiments. Modifications of the above-disclosed apparatus and methods which fall within the scope of this disclosure will be readily apparent to those of ordinary skill in the art.

What is claimed is:

1. A continuous analyte monitoring wearable device, comprising:
 a base unit, comprising:
  a base, at least one power source, and an analyte sensor assembly; and
  an encapsulation extending over the base and the at least one power source to form an encapsulated base, the encapsulated base including an attachment region configured to allow a reusable transmitter unit to be directly coupled to, and decoupled from, the encapsulated base,
wherein the reusable transmitter unit is configured to receive power from the at least one power source and to connect to the analyte sensor assembly when coupled to the attachment region;
wherein the encapsulated base, the at least one power source, and the analyte sensor assembly form a disposable unit, and the disposable unit is sterilized;
wherein the base comprises a transmitter unit support location configured to receive the reusable transmitter unit,
wherein the base comprises abase opening configured for receiving the reusable transmitter unit into the transmitter unit support location through the base opening, and
wherein the base opening is provided at a base side configured to be adjacent a user's skin when in use.

2. The continuous analyte monitoring wearable device of claim 1, wherein the base comprises sensor assembly support location configured to receive the analyte sensor assembly.

3. The continuous analyte monitoring wearable device of claim 1, wherein the base comprises a power source support location configured to receive the at least one power source.

4. The continuous analyte monitoring wearable device of claim 1, wherein the disposable unit is sterilized with electron beam radiation.

5. The continuous analyte monitoring wearable device of claim 1, wherein the disposable unit is sterilized by being irradiated with from 18 kGy to 25 kGy of electron beam radiation.

6. The continuous analyte monitoring wearable device of claim 1, wherein the attachment region has the reusable transmitter unit coupled thereto.

7. The continuous analyte monitoring wearable device of claim 1, wherein the base unit includes a connector that is configured to make electrical connection with and power the reusable transmitter unit when positioned at the attachment region.

8. The continuous analyte monitoring wearable device of claim 1, wherein the base unit includes a connector that is configured to make electrical connection between the reusable transmitter unit and the at least one power source.

9. The continuous analyte monitoring wearable device of claim 1, wherein the analyte sensor assembly includes an analyte sensor configured to sense an analyte concentration in an interstitial fluid.

10. The continuous analyte monitoring wearable device of claim 1, wherein the attachment region is configured to allow the reusable transmitter unit to removably couple to and seal a connector.

11. The continuous analyte monitoring wearable device of claim 1, wherein the disposable unit is packaged in a plastic housing having a removable plastic seal, foil seal, or other sealing cover after being sterilized.

12. The continuous analyte monitoring wearable device of claim 1, wherein the disposable unit, after being sterilized, is received and sealed in a laminated foil and plastic sheet enclosure.

13. A method of forming a continuous analyte monitoring wearable device, comprising:
providing a base having a power source support location, a sensor assembly support location, and a transmitter unit support location;
placing at least one power source at the power source support location,
wherein the at least one power source is configured to contact one or more electrical contacts attached to the power source support location;
placing a sensor assembly including an analyte sensor at the sensor assembly support location;
providing an encapsulation layer over the at least one power source, at least a portion of the sensor assembly, and at least a portion of the base, to form a sealed, disposable unit, wherein the sealed, disposable unit is configured to allow a transmitter unit to be attached to, and detached from, the transmitter unit support location at the base;
providing the transmitter unit to the transmitter unit support location at the base through a base opening,
wherein the base opening is provided at a base side configured to be adjacent a user's skin when in use; and
sterilizing the sealed, disposable unit.

14. The method of claim 13, wherein the encapsulation layer comprises an attachment region and the transmitter unit is first coupled to, and then decoupled from, the transmitter unit support location.

15. The method of claim 13, wherein the sterilizing of the sealed, disposable unit comprises subjecting the sealed, disposable unit to electron beam radiation.

16. The method of claim 15, wherein the sterilizing of the sealed, disposable unit comprises irradiating the sealed, disposable unit with from 18 kGy to 25 kGy of electron beam radiation.

17. The method of claim 13, wherein the providing the encapsulation layer includes forming the encapsulation layer at a temperature of less than 100° C.

18. The method of claim 13, comprising packaging the sealed, disposable unit in a plastic housing having a sealing cover, or sealed in a laminated foil and plastic sheet enclosure.

19. A method of forming a wearable device configured to be used in continuous analyte monitoring, comprising:
providing a base having a transmitter unit support location, a power source support location, and a sensor assembly support location;
placing at least one power source at the power source support location,
wherein the at least one power source is configured to contact one or more electrical contacts attached to the power source support location;
placing a sensor assembly including an analyte sensor at the sensor assembly support location;
providing an encapsulation portion having an opening;
placing the base within the opening of the encapsulation portion such that the base and encapsulation portion form a sealed, disposable base unit, wherein the sealed, disposable base unit is configured to allow a transmitter unit to be attached to and detached from the transmitter unit support location at the base;
providing the transmitter unit to the transmitter unit support location at the base through a base opening,
wherein the base opening is provided at a base side configured to be adjacent a user's skin when in use; and
sterilizing the sealed, disposable unit.

20. The method of claim 19, wherein the analyte sensor is configured to sense an analyte concentration in an interstitial fluid.

* * * * *